United States Patent
Osawa et al.

(10) Patent No.: US 8,527,296 B2
(45) Date of Patent: Sep. 3, 2013

(54) MEDICAL INFORMATION PROCESSING SYSTEM, MEDICAL INFORMATION PROCESSING METHOD, AND COMPUTER READABLE MEDIUM

(75) Inventors: Akira Osawa, Tokyo (JP); Shoji Hara, Tokyo (JP); Yasuhiko Kaneko, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 474 days.

(21) Appl. No.: 12/238,047

(22) Filed: Sep. 25, 2008

(65) Prior Publication Data

US 2009/0083072 A1 Mar. 26, 2009

(30) Foreign Application Priority Data

Sep. 26, 2007 (JP) .................................. 2007-249306
Jul. 24, 2008 (JP) .................................. 2008-190974

(51) Int. Cl.
*G06Q 10/00* (2012.01)
(52) U.S. Cl.
USPC .................................................. 705/2; 705/3
(58) Field of Classification Search
USPC .......................................................... 705/2
See application file for complete search history.

(56) References Cited

U.S. PATENT DOCUMENTS

| | | | |
|---|---|---|---|
| 6,234,964 B1* | 5/2001 | Iliff | 600/300 |
| 6,238,342 B1* | 5/2001 | Feleppa et al. | 600/437 |
| 2004/0120580 A1 | 6/2004 | Sabol et al. | |
| 2009/0228299 A1* | 9/2009 | Kangarloo et al. | 705/2 |

FOREIGN PATENT DOCUMENTS

| | | |
|---|---|---|
| JP | 05-101122 A | 4/1993 |
| JP | 6292656 A | 10/1994 |
| JP | 2001331581 A | 11/2001 |
| JP | 2002230518 A | 8/2002 |
| JP | 2004-199691 A | 7/2004 |
| JP | 2006085545 A | 3/2006 |
| JP | 2006155002 A | 6/2006 |
| JP | 2006181037 A | 7/2006 |

OTHER PUBLICATIONS

Notification of Reasons for Refusal, dated Nov. 6, 2012, issued in corresponding JP Application No. 2008-190974, 5 pages in English and Japanese.

* cited by examiner

*Primary Examiner* — Hiep V Nguyen
(74) *Attorney, Agent, or Firm* — Sughrue Mion, PLLC

(57) ABSTRACT

There is provided a medical information processing system including a diagnosis information storing section that stores thereon frequency information in association with an initial diagnosis and a conclusive diagnosis, where the frequency information indicates a frequency with which a combination of the initial diagnosis and the conclusive diagnosis that is different from the initial diagnosis is observed, a diagnosis receiving section that receives a diagnosis during a diagnosis process, and a disease information presenting section that presents, to a diagnosis-making person, one of the conclusive diagnosis and the initial diagnosis which is stored on the diagnosis information storing section in association with one of the initial diagnosis and the conclusive diagnosis which is the same as the diagnosis received by the diagnosis receiving section, in a manner according to the frequency information stored on the diagnosis information storing section in association with the initial diagnosis and the conclusive diagnosis.

20 Claims, 15 Drawing Sheets

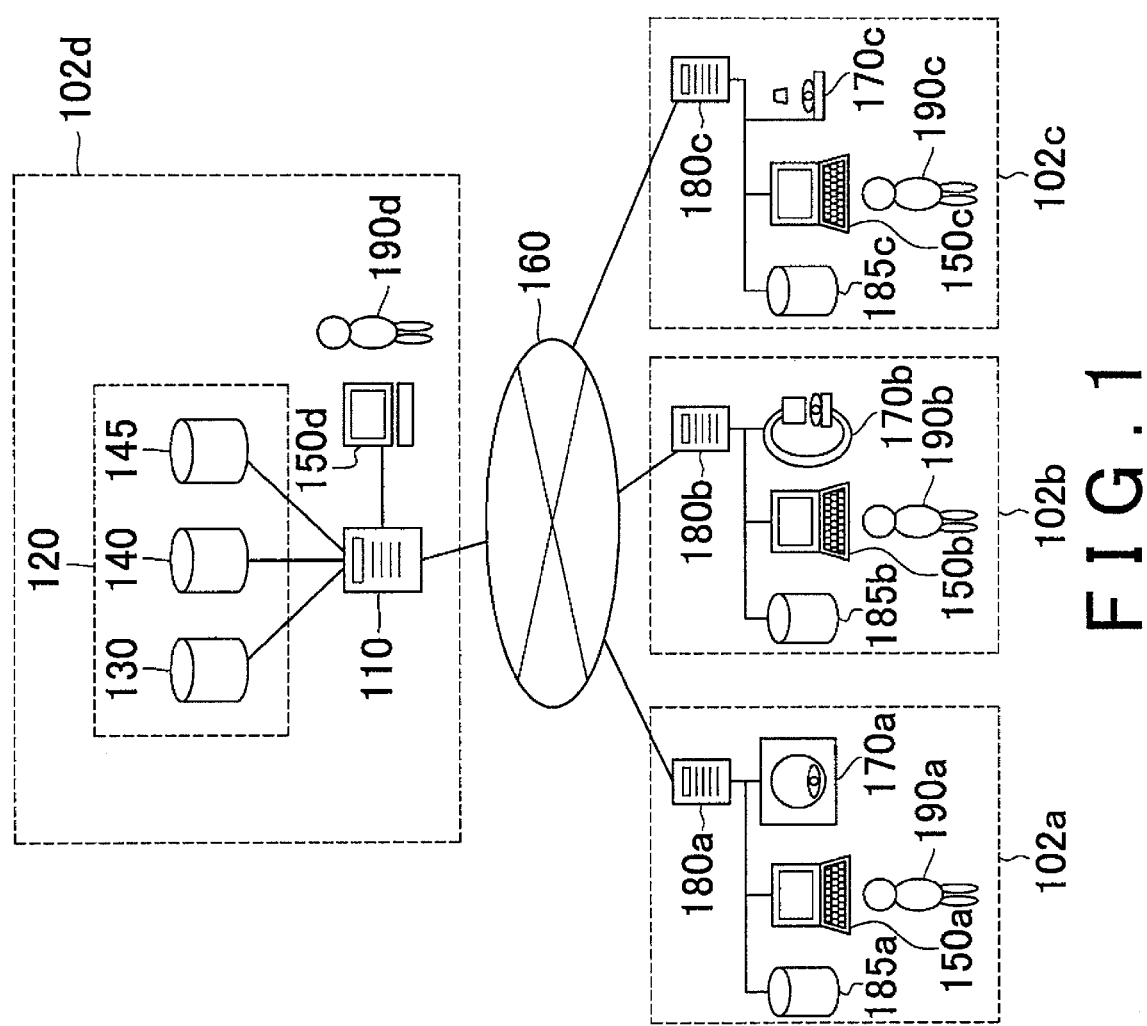

130

| DISEASE ID | IMAGE ID | DISEASE INFO DATA |
|---|---|---|
| #AAA | #aaa | aaa.dat |
| #BBB | #bbb | bbb.dat |
| #CCC | #ccc | ccc.dat |
| ⋮ | ⋮ | ⋮ |

F I G . 3

140

| USER ID | IMAGE ID | DISEASE ID | DIAGNOSIS DATA |
|---------|----------|------------|----------------|
| #d001 | #P001a | #AAA | C001.dat |
| #d002 | #P002a | #BBB | C002.dat |
| ⋮ | ⋮ | ⋮ | ⋮ |

| IMAGE ID | RADIOLOGY DEPARTMENT | | | REQUESTING DEPARTMENT | | | CONCLUSIVE DIAGNOSIS |
| --- | --- | --- | --- | --- | --- | --- | --- |
| | DIAGNOSIS-MAKING PERSON ID | DIAGNOSIS | REFERENCE CASE IMAGE ID | DIAGNOSIS-MAKING PERSON ID | DIAGNOSIS | REFERENCE CASE IMAGE ID | |
| #xxx | #d001 | #AAA | #P001a | #d010 | #BBB | #P002a | #BBB |
| #yyy | #d002 | #AAA | #P001a | #d011 | #CCC | #ccc | #CCC |
| ... | ... | ... | ... | ... | ... | ... | ... |

F I G . 5

| DIAGNOSIS-MAKING PERSON ID | INITIAL DIAGNOSIS | CONCLUSIVE DIAGNOSIS | NUMBER OF CASES |
|---|---|---|---|
| #d001 | #AAA | #AAA | 66 |
| #d001 | #AAA | #BBB | 10 |
| #d001 | #AAA | #CCC | 4 |
| #d002 | #AAA | #AAA | 80 |
| ⋮ | ⋮ | ⋮ | ⋮ |

FIG. 6

○ LUNG ADENOCARCINOMA IS MISDIAGNOSIS
　　　WITH PROBABILITY OF ○×%
CONCLUSIVE DIAGNOSIS INDICATES: ⎫
1. DISEASE A 5% OF THE TIME         ⎬ 810
2. DISEASE B 3% OF THE TIME         ⎭

○ WHEN THIS CASE IMAGE IS REFERRED TO,
　　LIKELIHOOD OF MISDIAGNOSIS IS ×△%
CONCLUSIVE DIAGNOSIS INDICATES: ⎫
1. DISEASE B 4% OF THE TIME         ⎬ 820
2. DISEASE A 3% OF THE TIME         ⎭

○ MISDIAGNOSIS RATE OF LUNG
　　ADENOCARCINOMA IS △○%
INITIAL DIAGNOSIS INDICATES: ⎫
1. DISEASE A 4% OF THE TIME   ⎬ 830
2. DISEASE C 2% OF THE TIME   ⎭

(CLOSE)

800

F I G . 8

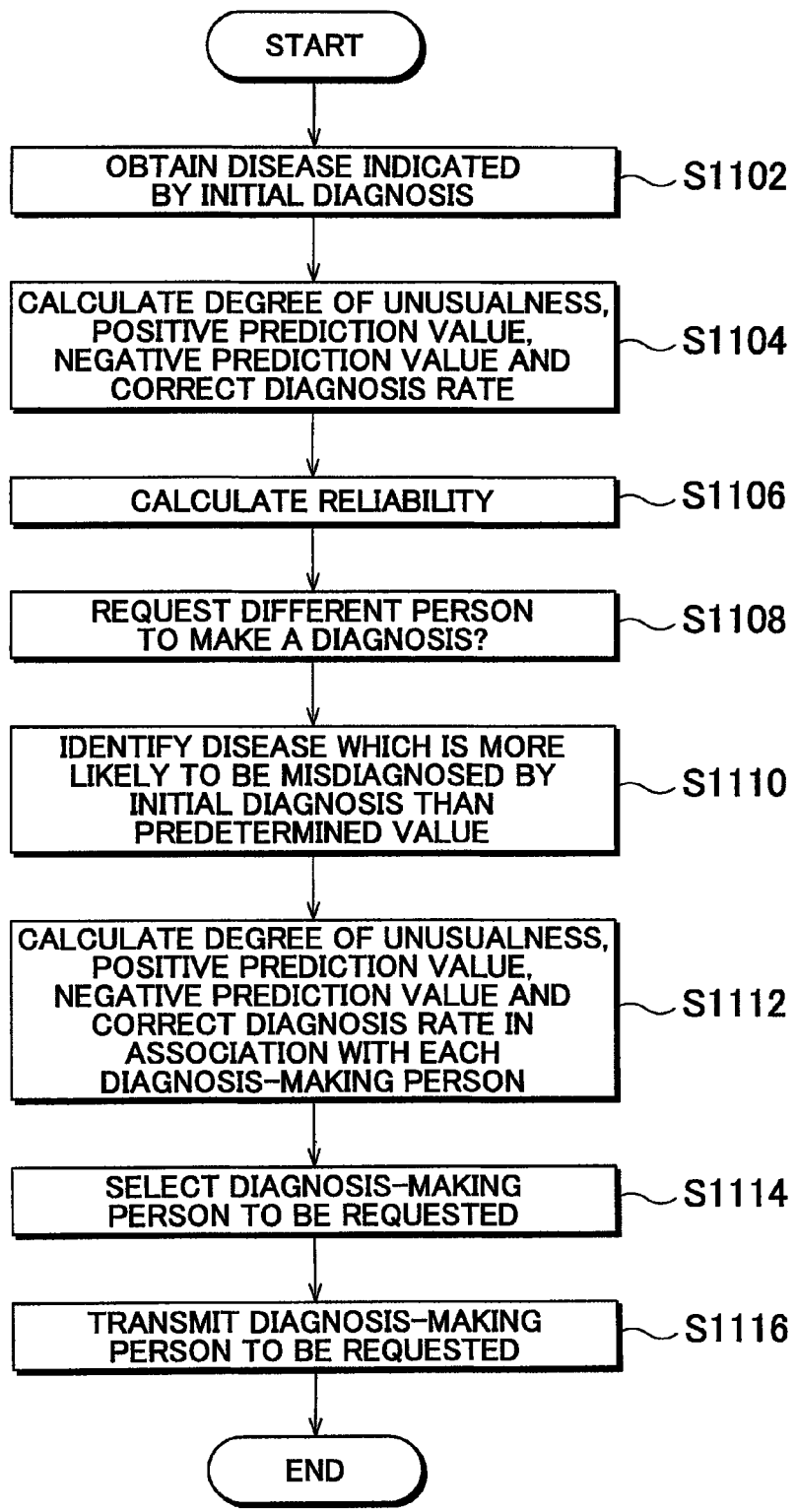
F I G. 11

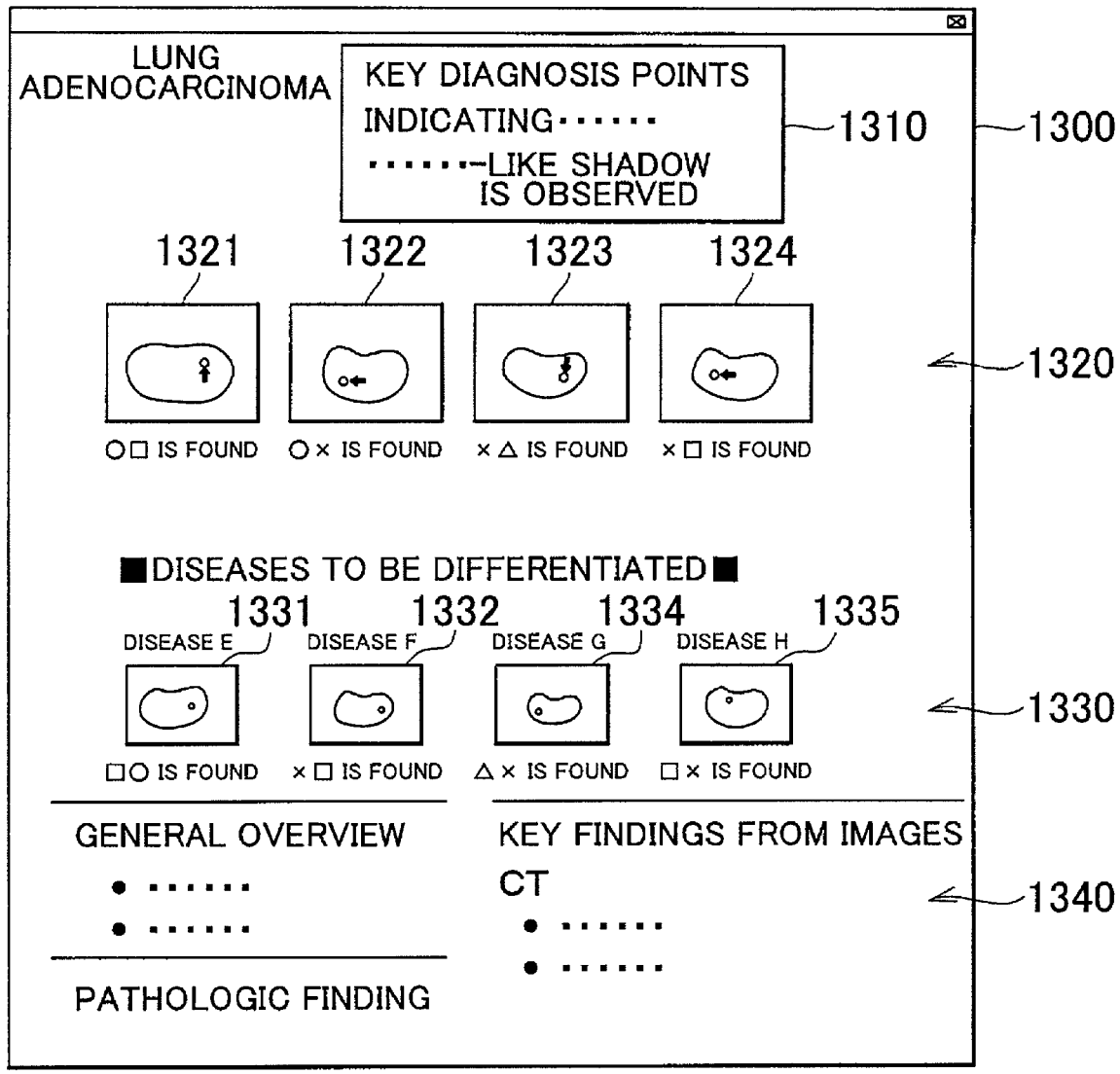
F I G . 13

MEDICAL INFORMATION PROCESSING SYSTEM, MEDICAL INFORMATION PROCESSING METHOD, AND COMPUTER READABLE MEDIUM

CROSS REFERENCE TO RELATED APPLICATION

The present application claims priority from Japanese Patent Applications No. 2007-249306 filed on Sep. 26, 2007 and No. 2008-190974 filed on Jul. 24, 2008, the contents of which are incorporated herein by reference.

BACKGROUND

1. Technical Field

The present invention relates to a medical information processing system, a medical information processing method, and a computer readable medium. More particularly, the present invention relates to a medical information processing system and a medical information processing method for processing medical information, and to a computer readable medium storing thereon a program for use with the medical information processing system.

2. Related Art

A known reference case retrieval technique records diagnosis history information including a radiogram interpretation by a radiology department, a diagnosis made by a particular department which has requested radiogram, a diagnosis made by means of CAD and a final and conclusive diagnosis, and can display the images of reference cases including cases where different persons make different diagnoses, on terminals in response to simple designation at the terminals, for example, as disclosed in Japanese Patent Application Publication No. 05-101122. Also, another known method automatically checks conclusions drawn by a plurality of readers who read the same medical image or the like, for example, as disclosed in Japanese Patent Application Publication No. 2004-199691.

According to the retrieval technique disclosed in Publication No. 05-101122, when the radiogram interpretation by the radiology department, the diagnosis made by the requesting department, and the diagnosis made by means of CAD are the same as the conclusive diagnosis, such a case is not stored on the reference case database. Therefore, the technique disclosed in Publication No. 05-101122 cannot inform diagnosis-making persons of how likely it is that a given initial diagnosis is a misdiagnosis. The technique disclosed in Publication No. 2004-199691 can display, in pop-up windows, different opinions when a plurality of medical doctors make different diagnoses. This technique, however, cannot inform diagnosis-making persons of how likely it is that a particular medical doctor makes a misdiagnosis according to the record of his/her past diagnoses.

SUMMARY

Therefore, it is an object of an aspect of the innovations herein to provide a medical information processing system, a medical information processing method, and a computer readable medium which are capable of overcoming the above drawbacks accompanying the related art. The above and other objects can be achieved by combinations described in the independent claims. The dependent claims define further advantageous and exemplary combinations of the innovations herein.

According to the first aspect related to the innovations herein, one exemplary medical information processing system may include a diagnosis information storing section that stores thereon frequency information in association with an initial diagnosis and a conclusive diagnosis, where the frequency information indicates a frequency with which a combination of the initial diagnosis and the conclusive diagnosis that is different from the initial diagnosis is observed, a diagnosis receiving section that receives a diagnosis during a diagnosis process, and a disease information presenting section that presents, to a diagnosis-making person, one of the conclusive diagnosis and the initial diagnosis which is stored on the diagnosis information storing section in association with one of the initial diagnosis and the conclusive diagnosis which is the same as the diagnosis received by the diagnosis receiving section, in a manner according to the frequency information stored on the diagnosis information storing section in association with the initial diagnosis and the conclusive diagnosis.

According to the second aspect related to the innovations herein, one exemplary medical information processing method may include storing frequency information in association with an initial diagnosis and a conclusive diagnosis, where the frequency information indicates a frequency with which a combination of the initial diagnosis and the conclusive diagnosis that is different from the initial diagnosis is observed, receiving a diagnosis during a diagnosis process, and presenting, to a diagnosis-making person, one of the conclusive diagnosis and the initial diagnosis which is stored in the storing in association with one of the initial diagnosis and the conclusive diagnosis which is the same as the diagnosis received in the receiving, in a manner according to the frequency information stored in the storing in association with the initial diagnosis and the conclusive diagnosis.

According to the third aspect related to the innovations herein, one exemplary computer readable medium may store thereon a program for use with a medical information processing system. Here, the program causes the medical information processing system to function as a diagnosis information storing section that stores thereon frequency information in association with an initial diagnosis and a conclusive diagnosis, where the frequency information indicates a frequency with which a combination of the initial diagnosis and the conclusive diagnosis that is different from the initial diagnosis is observed, a diagnosis receiving section that receives a diagnosis during a diagnosis process, and a disease information presenting section that presents, to a diagnosis-making person, one of the conclusive diagnosis and the initial diagnosis which is stored on the diagnosis information storing section in association with one of the initial diagnosis and the conclusive diagnosis which is the same as the diagnosis received by the diagnosis receiving section, in a manner according to the frequency information stored on the diagnosis information storing section in association with the initial diagnosis and the conclusive diagnosis.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 1 illustrates how a medical information processing system 100 relating to an embodiment of the present invention is used, as an example.

FIG. 3 illustrates an example of the data stored on a medical information database 130 by using a table.

FIG. 4 illustrates an example of the data stored on a case database 140 by using a table.

FIG. 5 illustrates an example of the data stored on a diagnosis database 145 by using a table.

FIG. 6 illustrates an example of another data stored on the diagnosis database 145 by using a table.

FIG. 8 illustrates an example of the misdiagnosis information displayed on the radiogram interpreter terminal 150 by the medical information processing apparatus 110.

FIG. 11 illustrates an exemplary flow of operations performed by the medical information processing apparatus 110 after obtaining an initial diagnosis.

FIG. 13 illustrates an example of the disease information displayed on the radiogram interpreter terminal 150 by the medical information processing apparatus 110.

DESCRIPTION OF EXEMPLARY EMBODIMENTS

Figure 2A:
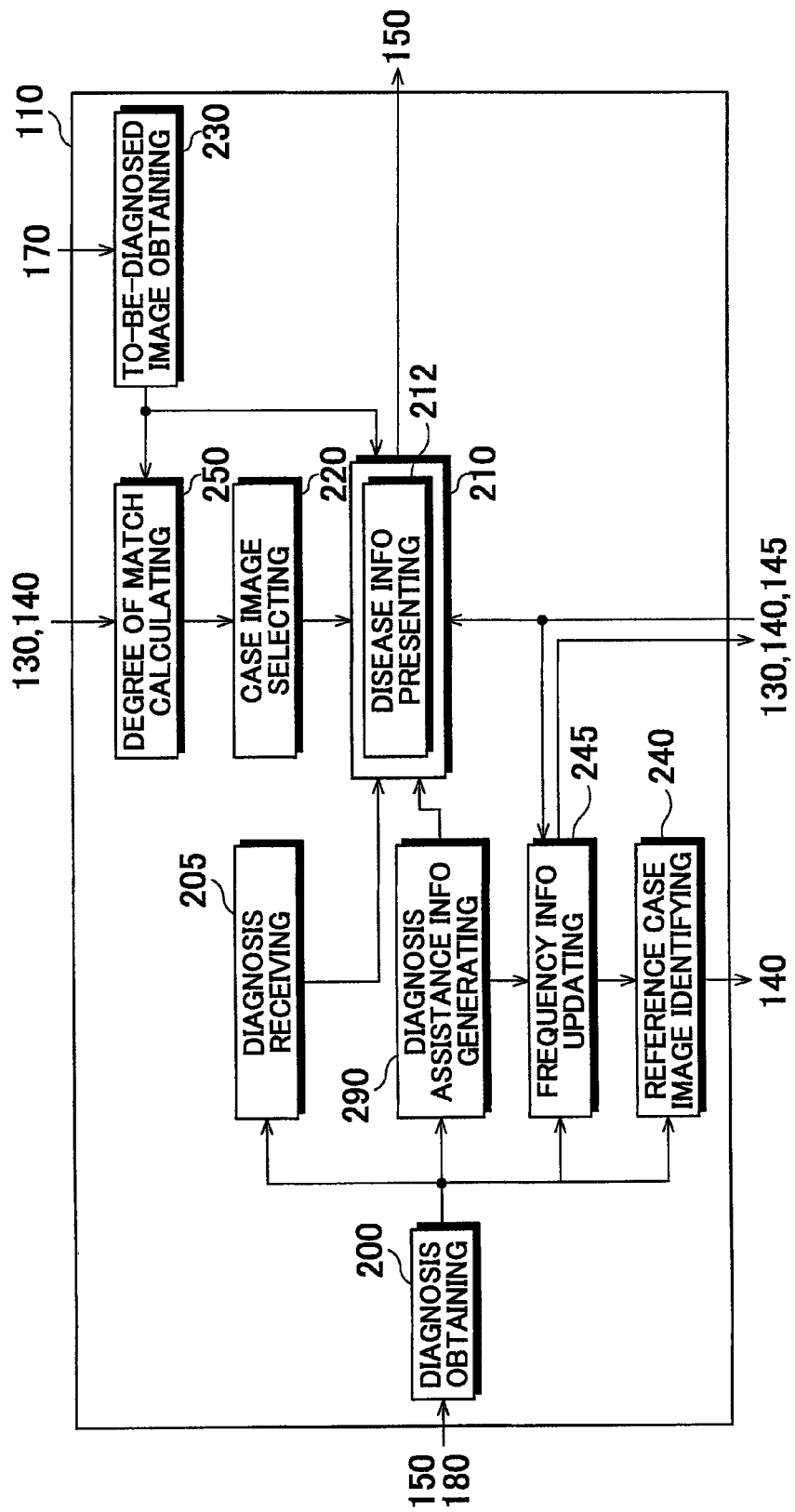
FIG. 2A illustrates an exemplary block configuration of a medical information processing apparatus 110.

Some aspects of the invention will now be described based on the embodiments, which do not intend to limit the scope of the present invention, but exemplify the invention. All of the features and the combinations thereof described in the embodiments are not necessarily essential to the invention.

FIG. 1 illustrates how a medical information processing system 100 relating to an embodiment of the present invention is used, as an example. The medical information processing system 100 includes a medical information processing apparatus 110, a diagnosis assistance information database 120, a plurality of case information servers 180a to 180c (hereinafter collectively referred to as the case information server 180), a plurality of case information databases 185a to 185c (hereinafter collectively referred to as the case information database 185), a plurality of radiogram interpreter terminals 150a to 150d (hereinafter referred to as the radiogram interpreter terminal 150), and a plurality of medical image capturing apparatuses 170a to 170c (hereinafter collectively referred to as the medical image capturing apparatus 170). The diagnosis assistance information database 120 includes a medical information database 130, a case database 140 and a diagnosis database 145.

The case information server 180a, case information database 185a, radiogram interpreter terminal 150a and medical image capturing apparatus 170a are provided in a diagnosis station 102a. The radiogram interpreter terminal 150a enables a radiogram interpreter 190a to interpret a to-be-interpreted image captured by the medical image capturing apparatus 170a. The case information server 180b, case information database 185b, radiogram interpreter terminal 150b and medical image capturing apparatus 170b are provided in a diagnosis station 102b. The radiogram interpreter terminal 150b enables a radiogram interpreter 190b to interpret a to-be-interpreted image captured by the medical image capturing apparatus 170b. The case information server 180c, case information database 185c, radiogram interpreter terminal 150c and medical image capturing apparatus 170c are provided in a diagnosis station 102c. The radiogram interpreter terminal 150c enables a radiogram interpreter 190c to interpret a to-be-interpreted image captured by the medical image capturing apparatus 170c. For example, the diagnosis stations 102a, 102b and 102c may be medical institutions such as hospitals different from each other. Each of the diagnosis stations 102a, 102b and 102c determines whether an examinee, for example, a patient, is affected by any disease, and diagnoses the disease when the examinee is affected.

In one example, the radiogram interpreter 190a interprets a to-be-interpreted image of an examinee in response to a request by a given department. The radiogram interpreter terminal 150a obtains, from the radiogram interpreter 190a which is shown as an example of a diagnosis-making person, an initial diagnosis of the examinee which includes the interpretation made by the radiogram interpreter 190a, and stores the initial diagnosis onto the case information database 185a. When the given department makes a diagnosis of the examinee, the case information database 185a transmits the initial diagnosis to a terminal used by a diagnosis-making person at the given department. The given department similarly diagnoses the examinee, and the diagnosis made by the given department is stored onto the case information database 185a. After this, a final and conclusive diagnosis is made, for example, based on a pathology test. The case information database 185a obtains the conclusive diagnosis from the radiogram interpreter terminal 150a or the like, and stores the obtained conclusive diagnosis. The case information server 180a transmits, to the medical information processing apparatus 110, case information including the initial diagnosis and conclusive diagnosis which are stored on the case information database 185a, and the to-be-interpreted image of the examinee which is captured by the medical image capturing apparatus 170a.

Referring to the diagnosis stations 102b and 102c, the radiogram interpreters 190b and 190c make a diagnosis in a similar manner to the radiogram interpreter 190a at the diagnosis station 102a as described above. The constituents of the diagnosis stations 102b and 102c may have substantially the same functions and operations as the corresponding constituents of the diagnosis station 102a which are assigned the same reference numerals. Therefore, the functions and operations of the case information servers 180b and 180c, case information databases 185b and 185c, and medical image capturing apparatuses 170b and 170c are not explained here.

The medical information processing apparatus 110, diagnosis assistance information database 120, and radiogram interpreter terminal 150d are provided at a diagnosis station 102d different from the diagnosis stations 102a to 102c. The medical information processing apparatus 110 is connected to the case information server 180 via a communication line 160, and obtains case information from the case information server 180. By using the obtained case information, the medical information processing apparatus 110 updates the case database 140 and diagnosis database 145. In this way, the medical information processing apparatus 110 can collect case information from the case information servers 180a to 180c respectively provided at the diagnosis stations 102a to 102c, so that the diagnosis station 102d can serve as a single source of accumulating the case information.

The medical information processing apparatus 110 is connected to the medical image capturing apparatus 170 via the communication line 160 and case information server 180. In this manner, the medical information processing apparatus 110 collects the to-be-interpreted images captured by the medical image capturing apparatus 170 via the case information server 180, and stores the collected to-be-interpreted images onto the case database 140. The radiogram interpreter terminal 150d displays the to-be-interpreted images stored on the case database 140. With such a configuration, the radiogram interpreter terminal 150d can enable a radiogram interpreter 190d to interpret the to-be-interpreted images captured at the diagnosis stations 102a to 102c. The diagnosis station 102d may be an institution that provides a remote radiogram interpreting service. Also, the radiogram interpreter terminals 150a to 150c can obtain, via the communication line 160, the to-be-interpreted images stored on the case database 140, and can enable the radiogram interpreters 190a to 190c to interpret the obtained to-be-interpreted images.

The medical information database 130 stores medical information for assisting diagnosis-making persons to make a diagnosis, on a recording medium such as a hard disk or a non-volatile semiconductor memory that can electronically store the medical information. Here, the medical information includes descriptions of diseases, points to be checked during the interpretation of an image showing a lesion, points to be recorded as findings, and representative case images of respective diseases. The case database 140 stores a plurality of pieces of case information, on a recording medium such as a hard disk or a non-volatile semiconductor memory that can electronically store the case information. Here, the case information includes a medical record such as a case image, a finding, a symptom, a conclusive diagnosis, and chart data.

The medical information processing apparatus 110 is connected to the diagnosis assistance information database 120. The medical information processing apparatus 110 can electronically read/write the medical information stored on the medical information database 130, the case information stored on the case database 140, and the diagnosis information stored on the diagnosis database 145. The medical information processing apparatus 110 is connected to the radiogram interpreter terminal 150 via the communication line 160 or the like. In this manner, the medical information processing apparatus 110 electronically provides the medical information and case information read from the medical information database 130 and case database 140, to the radiogram interpreter terminal 150 via the communication line 160 or the like.

When a diagnosis is made, the radiogram interpreter terminal 150 obtains the to-be-interpreted image captured by the medical image capturing apparatus 170 and presents the obtained to-be-interpreted image to the radiogram interpreter 190. Here, the radiogram interpreter terminal 150 presents the related medical information, case information and diagnosis information which are obtained via the medical information processing apparatus 110, together with the to-be-interpreted image. The medical information processing apparatus 110 retrieves similar case images similar to the to-be-interpreted image to be interpreted by the radiogram interpreter 190 from the case database 140, and causes the radiogram interpreter terminal 150 to display the retrieved similar case images.

As stated above, the radiogram interpreter terminal 150 receives as input the initial diagnosis made by the radiogram interpreter 190, the conclusive diagnosis and the like, and transmits case information including the input initial and conclusive diagnoses and the to-be-interpreted image, to the medical information processing apparatus 110 directly or via the case information server 180 and the communication line 160. The medical information processing apparatus 110 stores the case information received from the radiogram interpreter terminal 150 or case information server 180, onto the case database 140 as a new piece of case information. In addition, the medical information processing apparatus 110 stores the initial and conclusive diagnoses included in the case information received from the case information server 180 or radiogram interpreter terminal 150, onto the diagnosis database 145 in association with a misdiagnosis frequency. When a diagnosis is made at the radiogram interpreter terminal 150, the medical information processing apparatus 110 calculates misdiagnosis indices, for example, misdiagnosis rates of the diseases shown by the similar case images based on the information stored on the diagnosis database 145, emphasizes disease information including the similar case images in accordance with the misdiagnosis indices, and causes the radiogram interpreter terminal 150 to display the emphasized disease information. The medical information processing apparatus 110 may emphasize a similar case image associated with a low misdiagnosis rate, when causing the radiogram interpreter terminal 150 to display the similar case images, for example.

The medical image capturing apparatus 170 may be implemented by an image capturing apparatus such as an X-ray CT scanner, a tomosynthesis apparatus and an MRI apparatus, which detects images of an examinee by using an electromagnetic wave including a radiation ray. In the above description, the medical information processing system 100 is configured so as to include a plurality of diagnosis stations 102. The medical information processing system 100, however, may be configured so as to include only a single diagnosis station 102. If such is the case, the diagnosis stations 102a to 102d may be different departments within a single medical institution. For example, the diagnosis stations 102a to 102d may be different specialties within a single medical institution.

When put into practical use, the medical information processing system 100 described above may function as a remote radiogram interpreting substitution system that substitutes for radiogram interpreting in a hospital short of radiogram interpreters, or as a second opinion provider system that can request a given hospital to provide a second opinion for a diagnosis made at a different hospital. When put into practical use, the medical information processing system 100 can electronically provide the radiogram interpreter terminal 150 with the medical information stored on the medical information database 130 and the case information stored on the case database 140. In other words, the medical information processing system 100 may function as electronic medical reference material to which cases can be dynamically added appropriately. The diagnosis database 145 is shown as an example of a diagnosis information storing section relating to the present invention, and the medical information database 130 and the case database 140 is shown as an example of a case image storing section relating to the present invention.

FIG. 2A illustrates an exemplary block configuration of the medical information processing apparatus 110. The medical information processing apparatus 110 includes a diagnosis obtaining section 200, a diagnosis receiving section 205, an output section 210, a case image selecting section 220, a to-be-diagnosed image obtaining section 230, a reference case image identifying section 240, a frequency information updating section 245, a degree of match calculating section 250, and a diagnosis assistance information generating section 290. The output section 210 includes a disease information presenting section 212.

The following describes the operations of the constituents of the medical information processing apparatus 110, in addition to the data stored on the diagnosis assistance information database 120. The functions and operations of the diagnosis assistance information generating section 290 are described later with reference to FIG. 2B.

The diagnosis database 145 stores frequency information indicating a frequency with which a combination of an initial diagnosis and a conclusive diagnosis different from the initial diagnosis is observed, in association with the initial and conclusive diagnoses. The diagnosis receiving section 205 receives a diagnosis when the diagnosis is made. For example, the diagnosis receiving section 205 obtains a diagnosis received by the diagnosis obtaining section 200 from the radiogram interpreter terminal 150 or case information server 180, and inputs the obtained diagnosis.

The disease information presenting section 212 presents, to the radiogram interpreter 190, a conclusive diagnosis or an initial diagnosis which is stored on the diagnosis database 145 in association with an initial diagnosis or a conclusive diagnosis that is the same as the diagnosis input by the diagnosis receiving section 205, in a manner according to frequency information that is stored on the diagnosis database 145 in association with the initial diagnosis and the conclusive diagnosis. For example, the disease information presenting section 212 may present, to the radiogram interpreter 190, a conclusive diagnosis or an initial diagnosis that is stored on the diagnosis database 145 in association with frequency information indicating that misdiagnoses have occurred, from among the conclusive diagnoses or the initial diagnoses that are stored on the diagnosis database 145 in association with the initial diagnosis or the conclusive diagnosis that is the same as the diagnosis input by the diagnosis receiving section 205.

Specifically speaking, the diagnosis database 145 stores frequency information indicating a frequency with which a combination of an initial diagnosis disease and a conclusive diagnosis disease that is different from the initial diagnosis disease is observed, in association with the initial diagnosis disease and the conclusive diagnosis disease. Here, the initial diagnosis disease is a disease indicated by an initial diagnosis and the conclusive diagnosis disease is a disease indicated by a conclusive diagnosis. The diagnosis receiving section 205 receives a disease whose disease information is to be presented to the radiogram interpreter 190 to make a diagnosis. The disease information presenting section 212 presents, to the radiogram interpreter 190, disease information of the conclusive diagnosis disease that is stored on the diagnosis database 145 in association with the initial diagnosis disease that is the same as the disease input by the diagnosis receiving section 205, in a manner according to the frequency information.

The medical information database 130 and case database 140 store case images to be presented to the radiogram interpreter 190 to make a diagnosis. The case image selecting section 220 selects case images to be referred to by the radiogram interpreter 190 to make a diagnosis, from among the case images stored on at least one of the medical information database 130 and case database 140. More specifically, the case image selecting section 220 selects case images which match a to-be-diagnosed image at a degree higher than a predetermined degree of match in terms of the characteristic values of the images, from among the case images stored on at least one of the medical information database 130 and case database 140. The to-be-diagnosed image is an image based on which a diagnosis is to be made. The disease information presenting section 212 presents the case images selected by the case image selecting section 220 to the radiogram interpreter 190 as the similar case images.

The diagnosis receiving section 205 receives the diseases indicated by the case images selected by the case image selecting section 220. Which is to say, the diagnosis receiving section 205 receives a disease related to a diagnosis target to be diagnosed by the radiogram interpreter 190. With the above-described configuration, the medical information processing apparatus 110 can promptly present, to the radiogram interpreter 190, disease information relating to the case images having characteristic values similar to the characteristic values of the to-be-interpreted image.

The reference case image identifying section 240 identifies a case image referred to by the radiogram interpreter 190 when making an initial diagnosis. The diagnosis database 145 stores frequency information in association with the referred case image identified by the reference case image identifying section 240, the initial diagnosis disease, and the conclusive diagnosis disease. The disease information presenting section 212 presents to the radiogram interpreter 190 the case images selected by the case image selecting section 220, and presents to the radiogram interpreter 190 the conclusive diagnosis disease or initial diagnosis disease that is stored on the diagnosis database 145 in association with the case image identified by the reference case image identifying section 240 and the initial diagnosis disease or conclusive diagnosis disease that is the same as the disease received by the diagnosis receiving section 205, in a manner according to the frequency information.

The case image selecting section 220 selects a case image that matches a to-be-diagnosed image at a degree higher than a predetermined degree of match in terms of the characteristic values of the images and that is stored on the diagnosis database 145 in association with frequency information satisfying a predetermined condition, from among the case images stored on the medical information database 130 or case database 140. For example, the case image selecting section 220 may select a case image that matches a to-be-diagnosed image at a degree higher than a predetermined degree of match in terms of the characteristic values of the images and that is stored on the diagnosis database 145 in association with frequency information indicating a lower frequency than a predetermined value, from among the case images stored on the medical information database 130 or case database 140. When the initial diagnosis disease that is the same as the disease input by the diagnosis receiving section 205 is associated with a plurality of conclusive diagnosis diseases on the diagnosis database 145, the disease information presenting section 212 may increase the degree of emphasis on the disease information of the diseases as the frequencies indicated by the frequency information associated with the diseases increase, and present the accordingly emphasized disease information to the radiogram interpreter 190.

The following describes the operations of the constituents of the medical information processing apparatus 110 when the medical information processing apparatus 110 obtains a new conclusive diagnosis. When the diagnosis obtaining section 200 obtains a new conclusive diagnosis, the frequency information updating section 245 may calculate the above-mentioned frequency, and update, with the calculated frequency, frequency information that is stored on the diagnosis database 145 in association with a conclusive diagnosis and an initial diagnosis.

Similarly to the medical information processing system 100 described earlier, when put into practical use, the medical information processing apparatus 110 may be capable of dynamically updating the frequency information and presenting to the radiogram interpreter 190 the disease information such as the similar case images in a manner according to the frequency information.

Figure 2B:
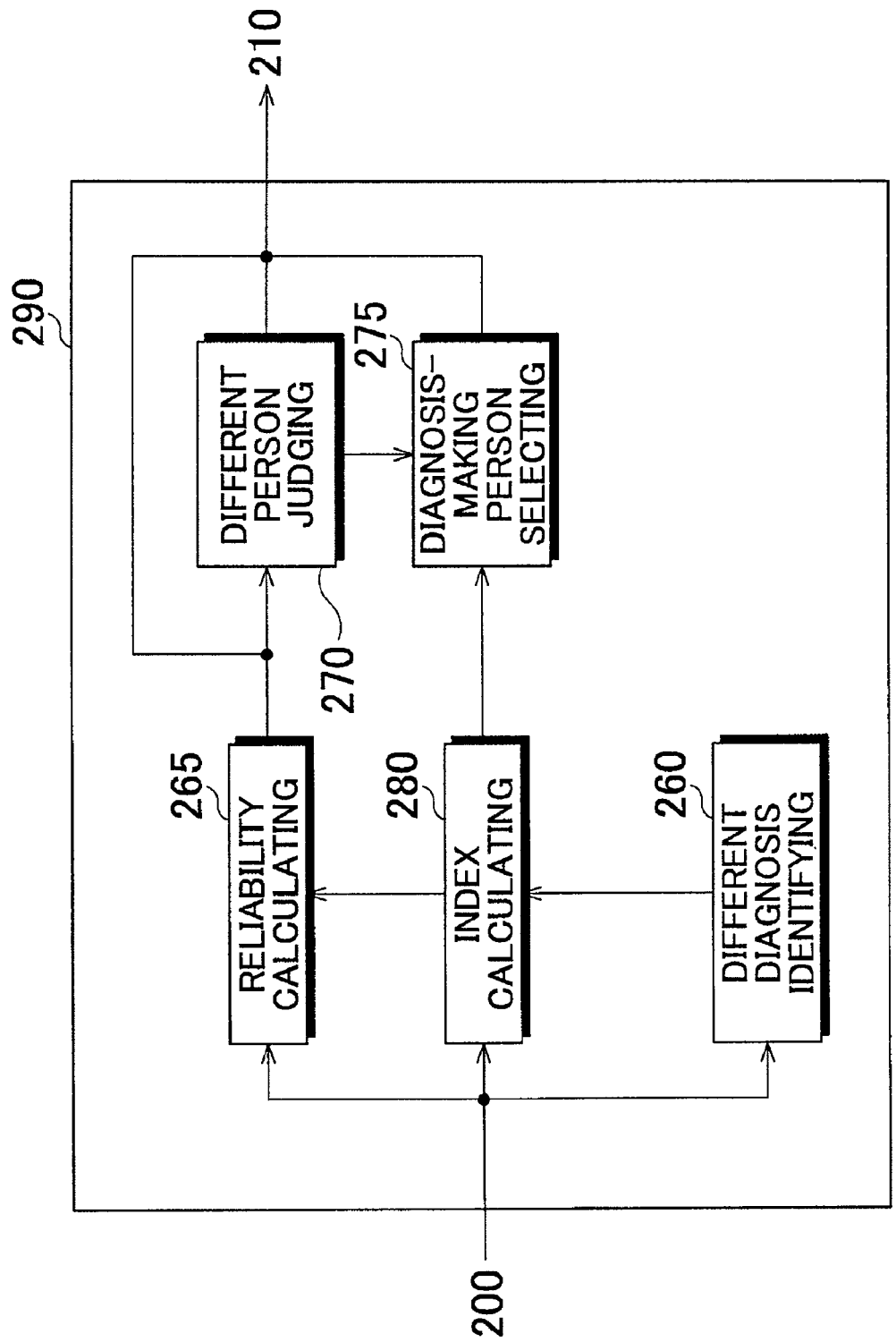
FIG. 2B illustrates an exemplary block configuration of a diagnosis assistance information generating section 290.

FIG. 2B illustrates an exemplary block configuration of the diagnosis assistance information generating section 290. The diagnosis assistance information generating section 290 calculates the reliability of an initial diagnosis obtained from the radiogram interpreter terminal 150, and provides the calculated reliability to the disease information presenting section 212. The diagnosis assistance information generating section 290 judges whether it is necessary to request a different diagnosis-making person to make a diagnosis based on the initial diagnosis obtained from the radiogram interpreter terminal 150, and provides the judgment to the disease information presenting section 212. The diagnosis assistance information generating section 290 selects a preferable different diagnosis-making person based on the initial diagnosis obtained from the radiogram interpreter terminal 150, and provides information indicating the selected diagnosis-making person to the disease information presenting section 212.

The diagnosis assistance information generating section 290 includes a different diagnosis identifying section 260, a reliability calculating section 265, a different person judging section 270, a diagnosis-making-person selecting section 275, and an index calculating section 280. The following describes the operations of the constituents of the diagnosis assistance information generating section 290 and the medical information processing apparatus 110, together with the data stored on the diagnosis assistance information database 120.

The diagnosis database 145 stores, in association with a radiogram interpreter 190, sameness information indicating a frequency with which initial diagnoses made by the radiogram interpreter 190 are the same as conclusive diagnoses. The diagnosis obtaining section 200 obtains a plurality of initial diagnoses respectively made by a plurality of radiogram interpreters 190 for the same diagnosis target. The reliability calculating section 265 calculates the reliability for each of the initial diagnoses obtained by the diagnosis obtaining section 200, based on the sameness information stored on the diagnosis database 145 in association with the radiogram interpreter 190 who has made the initial diagnosis. The output section 210 outputs each of the initial diagnoses obtained by the diagnosis obtaining section 200 in a manner according to the reliability calculated by the reliability calculating section 265 for the initial diagnosis.

The reliability calculating section 265 may increase the reliabilities of the initial diagnoses obtained by the diagnosis obtaining section 200, as the frequencies indicated by the pieces of sameness information stored on the diagnosis database 145 in association with the radiogram interpreters 190 who have made the obtained initial diagnoses increase.

The diagnosis database 145 may store, in association with a radiogram interpreter 190 and an initial diagnosis made by the radiogram interpreter 190, sameness information indicating a frequency with which the initial diagnosis made by the radiogram interpreter 190 is the same as a conclusive diagnosis. The reliability calculating section 265 increases the reliabilities of the initial diagnoses obtained by the diagnosis obtaining section 200, as the frequencies indicated by the pieces of sameness information that are stored on the diagnosis database 145 in association with the initial diagnoses and the radiogram interpreters 190 who have made the initial diagnoses increase.

The diagnosis database 145 may store, in association with an initial diagnosis, a conclusive diagnosis and a radiogram interpreter 190, sameness information indicating a frequency with which the conclusive diagnosis is made to a diagnosis target for which the radiogram interpreter 190 makes the initial diagnosis. The index calculating section 280 calculates an index indicating the appropriateness of each initial diagnosis for the radiogram interpreter 190 who makes the initial diagnosis, based on the sameness information stored on the diagnosis database 145 in association with the radiogram interpreter 190 who makes the initial diagnosis. The reliability calculating section 265 increases the reliability of the initial diagnosis, as the appropriateness of the initial diagnosis which is indicated by the index calculated by the index calculating section 280 increases.

The diagnosis database 145 may store, in association with an initial diagnosis, a conclusive diagnosis and a radiogram interpreter 190, the number of times at which the conclusive diagnosis is made to a diagnosis target for which the radiogram interpreter 190 makes the initial diagnosis. The index calculating section 280 calculates, for a radiogram interpreter 190 who makes each initial diagnosis, at least one of a degree of unusualness of the initial diagnosis, a positive prediction value for the initial diagnosis, a negative prediction value for the initial diagnosis and a correct diagnosis rate indicating the likelihood where the initial diagnosis made by the radiogram interpreter 190 is the same as a conclusive diagnosis, based on the information stored on the diagnosis database 145 in association with the radiogram interpreter 190 who makes the initial diagnosis. The reliability calculating section 265 increases the reliability of the initial diagnosis, as the degree of unusualness, positive prediction value, negative prediction value or correct diagnosis rate which is calculated by the index calculating section 280 for the initial diagnosis increases.

The following describes the functions and operations of the constituents of the diagnosis assistance information generating section 290 when the diagnosis assistance information generating section 190 generates information relating to a different diagnosis-making person. The different person judging section 270 uses the reliability of the initial diagnosis which is calculated by the reliability calculating section 265 in order to judge whether it is necessary to request a different one of a plurality of radiogram interpreters 190 to diagnose the same diagnosis target. When the different person judging section 270 judges that it is necessary to request a different radiogram interpreter 190 to diagnose the diagnosis target, the output section 210 outputs information indicating that it is necessary to request a different radiogram interpreter 190 to diagnose the diagnosis target.

When the different person judging section 270 judges that it is necessary to request a different radiogram interpreter 190 to diagnose the diagnosis target, the diagnosis-making-person selecting section 275 selects a different radiogram interpreter 190 who can diagnose the diagnosis target highly appropriately, based on initial diagnoses respectively made by a plurality of radiogram interpreters 190 and information stored on the diagnosis database 145 in association with the initial diagnoses or conclusive diagnoses that are the same as the initial diagnoses. When the different person judging section 270 judges that it is necessary to request a different radiogram interpreter 190 to diagnose the diagnosis target, the output section 210 outputs a different radiogram interpreter 190 selected by the diagnosis-making-person selecting section 275.

Specifically speaking, when the different person judging section 270 judges that it is necessary to request a different radiogram interpreter 190 to diagnose the diagnosis target, the index calculating section 280 calculates, for each radiogram interpreter 190 stored on the diagnosis database 145, at least one of the degree of unusualness, positive prediction value, negative prediction value and correct diagnosis rate for the diagnosis whose reliability is calculated by the reliability calculating section 265, based on the information stored on the diagnosis database 145. When the different person judging section 270 judges that it is necessary to request a different radiogram interpreter 190 to diagnose the diagnosis target, the diagnosis-making-person selecting section 275 increases the priority of an radiogram interpreter 190, as the degree of unusualness, positive prediction value, negative prediction value or correct diagnosis rate of the radiogram interpreter 190, which is calculated by the index calculating section 280, increases. With such a configuration, the diagnosis-making-person selecting section 275 can select a radiogram interpreter 190 who can appropriately diagnose whether the diagnosis target is affected by the disease indicated by the initial diagnosis.

Since the initial diagnosis is not necessarily the same as the conclusive diagnosis, the diagnosis-making-person selecting section 275 preferably selects a diagnosis-making person who can make an appropriate diagnosis about a suspected disease in addition to the disease indicated by the initial diagnosis. The following describes the functions and operations of the constituents of the diagnosis assistance information generating section 290 when the diagnosis assistance information generating section 290 selects a diagnosis-making person who can make such an appropriate diagnosis.

The different diagnosis identifying section 260 identifies a different diagnosis which is made as a conclusive diagnosis more frequently than a predetermined frequency when the initial diagnosis obtained by the diagnosis obtaining section 200 is made as an initial diagnosis, based on the information stored on the diagnosis database 145. When the different person judging section 270 judges that it is necessary to request a different radiogram interpreter 190 to diagnose the diagnosis target, the index calculating section 280 calculates, for each radiogram interpreter 190 stored on the diagnosis database 145, at least one of the degree of unusualness, positive prediction value, negative prediction value and correct diagnosis rate for the diagnosis which is identified by the different diagnosis identifying section 260, based on the information stored on the diagnosis database 145. When the different person judging section 270 judges that it is necessary to request a different radiogram interpreter 190 to diagnose the diagnosis target, the diagnosis-making person selecting section 275 increases the priority of a radiogram interpreter 190, as the degree of unusualness, positive prediction value, negative prediction value or correct diagnosis rate of the radiogram interpreter 190 which are calculated by the index calculating section 280 for the diagnosis identified by the different diagnosis identifying section 260 increases.

The different diagnosis identifying section 260 may identify, for each radiogram interpreter 190 who makes the initial diagnosis, a different diagnosis which is made as a conclusive diagnosis more frequently than a predetermined frequency when the initial diagnosis obtained by the diagnosis obtaining section 200 is made as an initial diagnosis, based on the information stored on the diagnosis database 145. The index calculating section 280 may extract a conclusive diagnosis and a frequency which are stored on the diagnosis database 145 in association with the radiogram interpreter 190 and the initial diagnosis made by the radiogram interpreter 190 and calculate, for each conclusive diagnosis, a total value obtained by adding together the extracted frequencies associated with a plurality of radiogram interpreters 190. The reliability calculating section 265 may increase the reliability for a conclusive diagnosis as the total value of the frequencies which is calculated by the index calculating section 280 for the conclusive diagnosis increases.

The present embodiment is described under the assumption that, when a disease of an initial diagnosis is different from a disease of a conclusive diagnosis, the initial diagnosis is a misdiagnosis. In the case of some diseases, a cytodiagnosis and the like needs to be performed to finally conclude whether the diseases are present and what types the diseases belong to. In addition, whether a disease is present and what type a disease belongs to may be finally concluded by a conference participated in by a plurality of medical doctors. The present embodiment is described under the assumption that a conclusive diagnosis is made by finally concluding whether a disease is present and what type a disease belongs to in the above-described manners. Furthermore, the present embodiment is described under the assumption that an initial diagnosis is any diagnosis made prior to the conclusive diagnosis or denotes the very first findings or the like made by a radiologist or the like.

Similarly to the medical information processing system 100 described with reference to FIG. 2B, when put into practical use, the medical information processing apparatus 110 may be capable of using the interpretation by a radiogram interpreter 190 to appropriately determine a different radiogram interpreter 190 who needs to cooperate in the interpretation of the to-be-interpreted image of the same diagnosis target. As a result, the medical information processing system 100 can promptly provide a diagnosis-making person with appropriate information in accordance with an initial diagnosis, based on the records of the past diagnoses.

FIG. 3 illustrates an example of the data stored on the medical information database 130 by using a table. The medical information database 130 stores medical information data, which is stored on electronic medical dictionaries.

Specifically speaking, the medical information database 130 stores a disease ID identifying a disease, an image ID identifying a case image showing the disease, and disease information data in association with each other. The case image stored on the medical information database 130 may be a representative case image of the disease. For example, the case image stored on the medical information database 130 may be a case image obtained from a paper medical reference material, and may be a case image showing a characteristic feature of the disease. The disease information data may include character information and image information to be provided to the radiogram interpreter 190 regarding the disease, for example the feature of the disease, the point to be noticed at the radiogram interpretation, the point to be recorded as a finding, a template sentence of the finding, and a different disease that is likely to be misdiagnosed. The disease information data may include a finding from the case image and a symptom of the disease.

FIG. 4 illustrates an example of the data stored on the case database 140 by using a table. The case database 140 stores an image captured by the medical image capturing apparatus 170 as a case image, in addition to a diagnosis made based on the captured image.

Specifically speaking, the case database 140 stores a user ID uniquely identifying the radiogram interpreter 190, an image ID identifying a case image captured by the medical image capturing apparatus 170, a disease ID identifying a disease, and diagnosis data in association with each other. The user ID may be information identifying a user who is allowed to use the case image stored on the case database 140.

As mentioned above, the case database 140 stores a case image in association with a user ID. Therefore, the case database 140 can accumulate case images in association with each radiogram interpreter 190. With such a configuration, the case database 140 can serve as a case database of each radiogram interpreter 190. Also, the medical information processing apparatus 110 may use the user ID as permission information in order to allow the use of the case image to a limited radiogram interpreter 190. In place of the user ID, the case database 140 may store information identifying a diagnosis station 102. In this manner, the case database 140 can serve as a case database of, for example, a particular hospital.

The image ID may be information identifying a case image stored on the case database 140. The image ID may be information identifying a case image stored on the case database 140 and a case image stored on the medical information database 130. The disease ID may identify a disease indicated by a conclusive diagnosis made for a diagnosis target shown in the corresponding case image.

The diagnosis data includes data recorded as a medical record. For example, the diagnosis data includes patient information obtained during a medical examination process, such as the name, sex, age, diagnosis and medication of a patient, in other words, medical examination information or medical service information. Specifically speaking, the diagnosis data may be medical chart data. The case database 140 may store, in association with each radiogram interpreter 190 identified by a user ID, diagnosis data including a diagnosis made by the radiogram interpreter 190.

The diagnosis included in the diagnosis data includes a finding acquired during the medical examination process and a symptom observed during the medical examination process. The finding included in the diagnosis data includes a finding made by the radiogram interpreter 190 by interpreting a to-be-interpreted image.

FIG. 5 illustrates an example of the data stored on the diagnosis database 145 by using a table. The diagnosis database 145 stores an image ID, a diagnosis, a diagnosis-making person ID, a reference case image ID and a conclusive diagnosis. Note that the diagnosis database 145 stores the diagnosis, diagnosis-making person ID and reference case image ID in association with each of a plurality of diagnosis-making persons (for example, a radiology department and a requesting department).

The image ID may be identification information identifying a to-be-interpreted image. The diagnosis may be a disease ID identifying a disease included in a diagnosis made by a radiogram interpreter 190 by interpreting the to-be-interpreted image including an image identified by the image ID. The diagnosis-making person ID may be identification information identifying the radiogram interpreter 190 who makes the diagnosis. The reference case image ID may be an image ID identifying a case image referred to by the radiogram interpreter 190 who makes the diagnosis during the radiogram interpretation from among the case images stored on at least one of the medical information database 130 and case database 140. The conclusive diagnosis may be a disease ID identifying a disease included in a conclusive diagnosis.

FIG. 6 illustrates an example of another data stored on the diagnosis database 145 by using a table. The diagnosis database 145 stores a diagnosis-making person ID, an initial diagnosis, a conclusive diagnosis, and the number of cases.

The diagnosis-making person ID may be identification information identifying a radiogram interpreter 190 as explained with reference to FIG. 5. The initial diagnosis may be a disease ID identifying a disease indicated by a diagnosis made before a conclusive diagnosis is made. The initial diagnosis includes a diagnosis made by the radiology department and a diagnosis made by the requesting department described with reference to FIG. 5.

The conclusive diagnosis may be a disease ID identifying a disease indicated by a conclusive diagnosis, as described with reference to FIG. 5. The number of cases may denote the number of times at which a given combination of the initial diagnosis made by the radiogram interpreter 190 identified by the diagnosis-making person ID and the conclusive diagnosis is observed. When obtaining a conclusive diagnosis, the diagnosis database 145 calculates the data shown in FIG. 6 based on the data described with reference to FIG. 5 in association with each radiogram interpreter 190 and stores the calculated data.

As stated above, the diagnosis database 145 stores, in association with each radiogram interpreter 190, the number of cases where a given combination of a particular initial diagnosis made by the radiogram interpreter 190 and a particular conclusive diagnosis is observed. Accordingly, the medical information processing apparatus 110 can calculate frequency information in association with each radiogram interpreter 190, in addition to overall frequency information in association with a plurality of radiogram interpreters 190, as described later.

As stated above, the diagnosis database 145 stores a value representing the number of times at which the disease of an initial diagnosis is the same as the disease of a conclusive diagnosis. Also, the diagnosis database 145 stores a value representing the number of times at which the disease of an initial diagnosis is different from the disease of a conclusive diagnosis. In the present embodiment, the frequency information may denote at least one of a same diagnosis case number indicating the number of times at which the initial and conclusive diagnoses indicate the same disease and a different diagnosis case number indicating the number of times at which the initial and conclusive diagnoses indicate different diseases. Another example of the frequency information can be the ratio of the same diagnosis case number to the total number or the ratio of the different diagnosis case number to the total number. Note that the total number may be defined as the sum of the same diagnosis case number and the different diagnosis case number. Here, the initial and conclusive diagnoses may include information indicating that no diseases are found.

As described with reference to FIGS. 3 to 6, the disease ID associates, to each other, the information stored on the diagnosis database 145, the diagnosis data stored on the case database 140, and disease information data stored on the medical information database 130. Therefore, the diagnosis database 145 stores an initial diagnosis disease, a conclusive diagnosis disease and frequency information, in association with a finding and a symptom observed by medical examination. As a result, the disease information presenting section 212 can present, to a diagnosis-making person, at least one of the finding and symptom of a conclusive diagnosis disease which is stored on the diagnosis database 145 in association with an initial diagnosis disease that is the same as the disease received by the diagnosis receiving section 205, based on the information stored on the diagnosis database 145, in a manner according to the frequency information.

Figure 7:
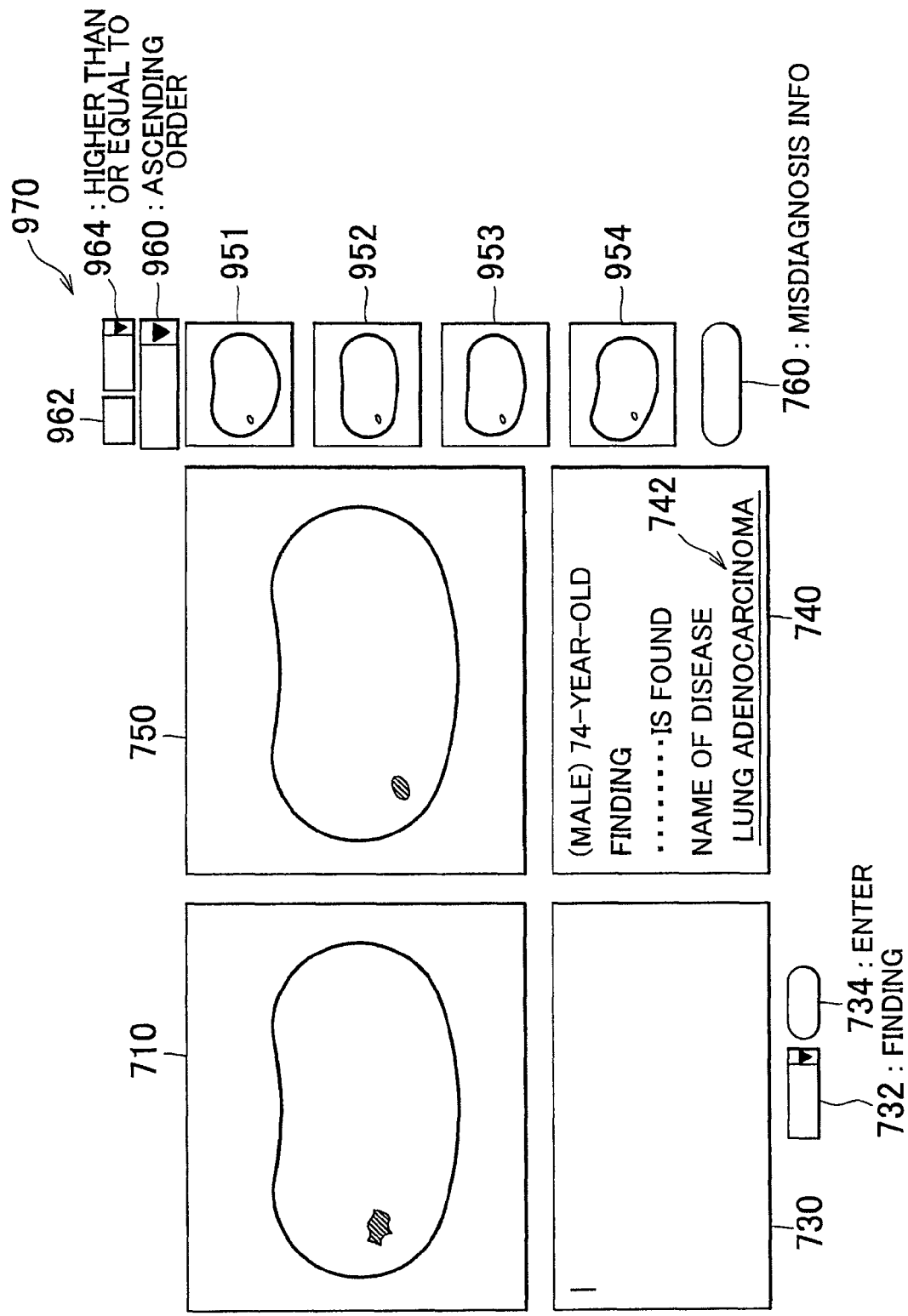
FIG. 7 illustrates an example of the screen displayed on a radiogram interpreter terminal 150 by the medical information processing apparatus 110.

FIG. 7 illustrates an example of the screen displayed on the radiogram interpreter terminal 150 by the medical information processing apparatus 110. The medical information processing apparatus 110 causes the radiogram interpreter terminal 150 to display a screen including a to-be-interpreted image window 710, a similar case image window 720, similar case image windows 951 to 954, a diagnosis report input window 730, a reference diagnosis report display window 740, a misdiagnosis information button 760, an input setting menu 732, a diagnosis input button 734, and a retrieval condition setting menu 950.

In the to-be-interpreted image window 710, the medical information processing apparatus 110 causes the radiogram interpreter terminal 150 to display a to-be-interpreted image obtained from the medical information processing apparatus 110. In the similar case image windows 951 to 953, the medical information processing apparatus 110 causes the radiogram interpreter terminal 150 to display the similar case images selected by the case image selecting section 220 from among the case images stored on the case database 140. In the similar case image window 954, the medical information processing apparatus 110 causes the radiogram interpreter terminal 150 to display a similar case image selected by the case image selecting section 220 from among the case images stored on the medical information database 130. When the radiogram interpreter 190 designates a case image by clicking one of the similar case image windows 951 to 954 with the use of a mouse or the like, the radiogram interpreter terminal 150 displays the designated case image in the similar case image window 750 in an enlarged state.

The medical information processing apparatus 110 retrieves diagnosis data or disease information data of the designated case image, such as a finding, from the case database 140 or medical information database 130, and causes the radiogram interpreter terminal 150 to display the retrieved data in the reference diagnosis report display window 740. Here, the medical information processing apparatus 110 causes the radiogram interpreter terminal 150 to display, in the reference diagnosis report display window 740, the disease included in the diagnosis data in the form of a link 742 to the disease information data stored on the medical information database 130. The link 742 may be a hyperlink in the hypertext written in, for example, HTML. When the radiogram interpreter 190 clicks the link 742 displayed on the radiogram interpreter terminal 150 by way of mouse manipulation or the like, the medical information processing apparatus 110 retrieves the linked disease information data from the medical information database 130, transmits the retrieved disease information data to the radiogram interpreter terminal 150, and causes the radiogram interpreter terminal 150 to display the disease information data. The disease information data may be described in any of the markup languages including HTML and XML.

When the radiogram interpreter 190 clicks the misdiagnosis information button 760 by way of mouse manipulation or the like, the medical information processing apparatus 110 causes the radiogram interpreter terminal 150 to display misdiagnosis information relating to the case image displayed in the similar case image window 750 and the diagnosis made based on the case image. The misdiagnosis information is described in detail with reference to FIG. 8. In this manner, the radiogram interpreter 190 can input a diagnosis including a disease into the diagnosis report input window 730 by referring to the to-be-interpreted image displayed in the to-be-interpreted image window 710, the similar case image displayed in the similar case image window 750, the diagnosis made based on the similar case image, and the misdiagnosis information.

The radiogram interpreter terminal 150 transmits, to the medial information processing apparatus 110, a disease ID identifying the disease included in the diagnosis input into the diagnosis report input window 730 by the radiogram interpreter 190, together with a diagnosis-making person ID identifying the radiogram interpreter 190 and a case image ID identifying the case image displayed in the similar case image window 750 by the radiogram interpreter 190. The medical information processing apparatus 110 stores the disease ID, diagnosis-making person ID and case image ID received from the radiogram interpreter terminal 150 onto the diagnosis database 145.

Specifically speaking, the medical information processing apparatus 110 stores, as a diagnosis, the disease ID received from the radiogram interpreter terminal 150 onto the diagnosis database 145 as described with reference to FIG. 5. Also, the medical information processing apparatus 110 stores, as a reference case image ID, the case image ID received from the radiogram interpreter terminal 150, onto the diagnosis database 145. The medical information processing apparatus 110 stores the diagnosis-making person ID received from the radiogram interpreter terminal 150 onto the diagnosis database 145.

The following describes the retrieval condition setting menu 970. The retrieval condition setting menu 970 may be a setting menu for setting a retrieval condition used for retrieving similar case images. Specifically speaking, the retrieval condition setting menu 970 may be a menu for setting a retrieval condition by using a misdiagnosis frequency indicated by frequency information as a parameter.

When the radiogram interpreter 190 changes the retrieval condition through the retrieval condition setting menu 970, the radiogram interpreter terminal 150 transmits the new retrieval condition to the medical information processing apparatus 110. When the medical information processing apparatus 110 receives the retrieval condition, the case image selecting section 220 selects case images satisfying the received retrieval condition as similar case image. The selected similar case images are transmitted to the radiogram interpreter terminal 150, to be displayed in the similar case image windows 951 to 954.

Specifically speaking, the retrieval condition setting menu 970 includes an order setting menu 960, a frequency input field 962, and a high or low setting menu 964. The order setting menu 960 enables the radiogram interpreter 190 to select whether to retrieve similar case images in accordance with the ascending or descending order of the misdiagnosis frequency. The case image selecting section 220 may select a predetermined number of case images as similar case images by referring to the information set by the order setting menu 960 and the frequency information stored on the diagnosis database 145.

The frequency input field 962 receives a threshold value of the misdiagnosis frequency. The case image selecting section 220 may select, as the similar case images, case images of diseases associated with frequency information indicating a frequency either no less than or no more than the value input into the frequency input field 962. Whether to select case images of diseases associated with misdiagnosis frequency either no less than or no more than the value input into the frequency input field 962 may be selected through the high or low setting menu 964.

The case database 140 may not store a sufficient number of cases of a certain disease. In this case, the misdiagnosis frequency of the disease is expected to be inaccurate. Therefore, when the number of cases is less than a predetermined number, the disease information presenting section 212 may cause the radiogram interpreter terminal 150 to display that information. For example, the disease information presenting section 212 may cause the radiogram interpreter terminal 150 to display the information indicating that the number of cases of a given disease is less than a predetermined number, in association with one of the similar case image windows 951 to 953 which displays the case image of the given disease. The disease information presenting section 212 may cause the radiogram interpreter terminal 150 to display the information indicating that the number of cases is less than a predetermined number, as part of the misdiagnosis information displayed on the radiogram interpreter terminal 150 when the misdiagnosis information button 760 is clicked. With such a configuration, the medical information processing system 100 may be capable of preventing the radiogram interpreter 190 from making a diagnosis by referring to misdiagnosis information of rare cases. The disease information presenting section 212 may cause the radiogram interpreter terminal 150 to display the number of cases as an index to be used for judging whether the number of cases is sufficient or not.

The case image selecting section 220 may select, as the similar case images, the case images of the diseases whose numbers of cases are more than a predetermined number, from among the case images stored on the case database 140. In this manner, the medical information processing system 100 can prevent the radiogram interpreter 190 from referring to similar case images of diseases whose numbers of cases are small, from the beginning. When the number of cases of a given disease that are stored on the case database 140 is less than a predetermined number, the case image selecting section 220 may not select a case image of the given disease that is stored on the case database 140 as a similar case image, but select a case image of the given image that is stored on the medical information database 130 as a similar case image.

According to the above-described exemplary embodiment, the reference diagnosis report display window 740 displays disease information of a disease relating to the similar case image selected by the radiogram interpreter 190. Alternatively, the radiogram interpreter terminal 150 may display, in the reference diagnosis report display window 740 or the like, disease information of a disease relating to the information directly input by the radiogram interpreter 190. Examples of the information directly input by the radiogram interpreter 190 may include a finding, a symptom, a disease and the like.

The input setting menu 732 selects which one of the finding, symptom and disease is to be directly input by the radiogram interpreter 190. A click of the diagnosis input button 734 transmits at least one of the finding, symptom and disease which is directly input by the radiogram interpreter 190 to the medical information processing apparatus 110.

For example, it is assumed that a finding is input into the diagnosis report input window 730 and that the input setting menu 732 selects the input of the finding. In this case, the radiogram interpreter terminal 150 transmits the finding input into the diagnosis report input window 730 to the medical information processing apparatus 110. At the medical information processing apparatus 110, the diagnosis receiving section 205 receives the finding received from the radiogram interpreter terminal 150. The disease information presenting section 212 retrieves a finding matching the finding received by the diagnosis receiving section 205 at a degree higher than a predetermined value and selects a disease for which the retrieved finding is observed, as a similar finding disease.

Specifically speaking, the disease information presenting section 212 can select the similar finding disease from the case database 140, by retrieving a finding matching the received finding at a degree higher than a predetermined value from the diagnosis data stored on the case database 140. The disease information presenting section 212 can select the similar finding disease from the medical information database 130 by retrieving a finding matching the received finding at a degree higher than a predetermined value from the disease information data stored on the medical information database 130.

The disease information presenting section 212 selects disease information of the conclusive diagnosis disease stored on the diagnosis database 145 in association with the initial diagnosis disease that is the same as the similar finding disease. The disease information presenting section 212 may extract the disease information from the diagnosis data stored on the case database 140 and the disease information data stored on the medical information database 130. Here, the disease information presenting section 212 may select disease information of a conclusive diagnosis disease associated with frequency information satisfying a predetermined condition. For example, the disease information presenting section 212 may increase the priority of disease information of a conclusive diagnosis disease, as the misdiagnosis frequency associated with the conclusive diagnosis disease increases.

The disease information presenting section 212 transmits the selected disease information to the radiogram interpreter terminal 150. The radiogram interpreter terminal 150 may display the disease information transmitted from the medical information processing apparatus 110, in the reference diagnosis report display window 740 or the like. In this manner, the disease information presenting section 212 can present, to the diagnosis-making person, the disease information of the conclusive diagnosis disease that is stored on the diagnosis database 145 in association with the initial diagnosis disease that is the same as the disease indicated by the finding received by the diagnosis receiving section 205, in a manner according to the frequency information.

In a manner similar to the above-described procedure, the disease information presenting section 212 can select disease information based on a symptom. For example, it is assumed that a symptom is input into the diagnosis report input window 730 and that the input setting menu 732 selects the input of the symptom. In this case, the radiogram interpreter terminal 150 transmits the symptom input into the diagnosis report input window 730 to the medical information processing apparatus 110. The diagnosis receiving section 205 receives the symptom observed by the radiogram interpreter 190 from the radiogram interpreter terminal 150. The disease information presenting section 212 retrieves a symptom matching the symptom received by the diagnosis receiving section 205 at a degree higher than a predetermined value and selects a disease for which the retrieved symptom is observed, as a similar symptom disease.

Specifically speaking, the disease information presenting section 212 can select the similar symptom disease from the case database 140, by retrieving a symptom matching the received symptom at a degree higher than a predetermined value from the diagnosis data stored on the case database 140. The disease information presenting section 212 can select the similar symptom disease from the medical information database 130, by retrieving a symptom matching the received symptom at a degree higher than a predetermined value from the disease information data stored on the medical information database 130.

The disease information presenting section 212 can select disease information of the conclusive diagnosis disease stored on the diagnosis database 145 in association with the initial diagnosis disease that is the same as the similar symptom disease. The operations performed by the constituents of the medical information processing system 100 after the selection of the disease based on the similar symptom disease are the same as the operations performed by the constituents after the disease information is selected based on the similar finding disease, and thus not explained here. In the above-described manner, the disease information presenting section 212 can present, to the diagnosis-making person, the disease information of the conclusive diagnosis disease that is stored on the diagnosis database 145 in association with the initial diagnosis disease that is the same as the disease indicated by the symptom received by the diagnosis receiving section 205, in a manner according to the frequency information.

When the radiogram interpreter 190 inputs a disease, the constituents of the medical information processing system 100 may perform the operations same as the operations performed by the constituents after the disease information presenting section 212 selects the similar finding disease based on the finding input by the radiogram interpreter 190. Therefore, the operations performed by the constituents when the radiogram interpreter 190 inputs a disease are not explained here.

Other than the finding directly input by the radiogram interpreter 190, the examples of the finding input into the diagnosis receiving section 205 may include a finding observed in a similar case selected by the radiogram interpreter 190. The finding observed in the similar case can be extracted from the diagnosis data or disease information data relating to the similar case. In this manner, the diagnosis receiving section 205 can receive a finding observed for an examinee whose case image is selected by the case image selecting section 220. The disease information presenting section 212 can then present, to the diagnosis-making person, disease information of the conclusive diagnosis disease that is stored on the diagnosis database 145 in association with the initial diagnosis disease that is the same as the disease indicated by the finding received by the diagnosis receiving section 205, in a manner according to the frequency information.

Other than the symptom directly input by the radiogram interpreter 190, the examples of the symptom input into the diagnosis receiving section 205 may include a symptom observed in a similar case selected by the radiogram interpreter 190. The symptom observed in the similar case can be extracted from the diagnosis data or disease information data of the similar case. In this manner, the diagnosis receiving section 205 can receive a symptom observed for an examinee whose case image is selected by the case image selecting section 220. The disease information presenting section 212 can then present, to the diagnosis-making person, disease information of the conclusive diagnosis disease that is stored on the diagnosis database 145 in association with the initial diagnosis disease that is the same as the disease indicated by the symptom received by the diagnosis receiving section 205, in a manner according to the frequency information.

FIG. 8 illustrates an example of the misdiagnosis information displayed on the radiogram interpreter terminal 150 by the medical information processing apparatus 110. The medical information processing apparatus 110 causes the radiogram interpreter terminal 150 to display a misdiagnosis information window 800 including misdiagnosis information 810, 820 and 830 indicating the details of the misdiagnosis.

The misdiagnosis information 810 includes the probability in which an initial diagnosis indicating the given disease diagnosed for the selected similar case image is a misdiagnosis and a different disease (with its probability) than the given disease which is indicated by the conclusive diagnosis made for the diagnosis target whose initial diagnosis indicates the given disease. The misdiagnosis information 820 includes the likelihood of misdiagnosis when the selected similar case image is referred to and a different disease (with its probability) than the given disease which is indicated by a conclusive diagnosis. The misdiagnosis information 830 includes the likelihood where an initial diagnosis for a diagnosis target whose conclusive diagnosis indicates the given disease diagnosed from the selected similar case image indicates a different disease from the given disease and the different disease (with its probability) than the given disease indicated by the initial diagnosis.

As described above, the medical information processing system 100 can provide the radiogram interpreter 190 with a variety of types of information based on the diagnosis made for the selected similar case image. The medical information processing apparatus 110 can generate the data used to display the above-described misdiagnosis information, based on the information described with reference to FIG. 6.

Figure 9:
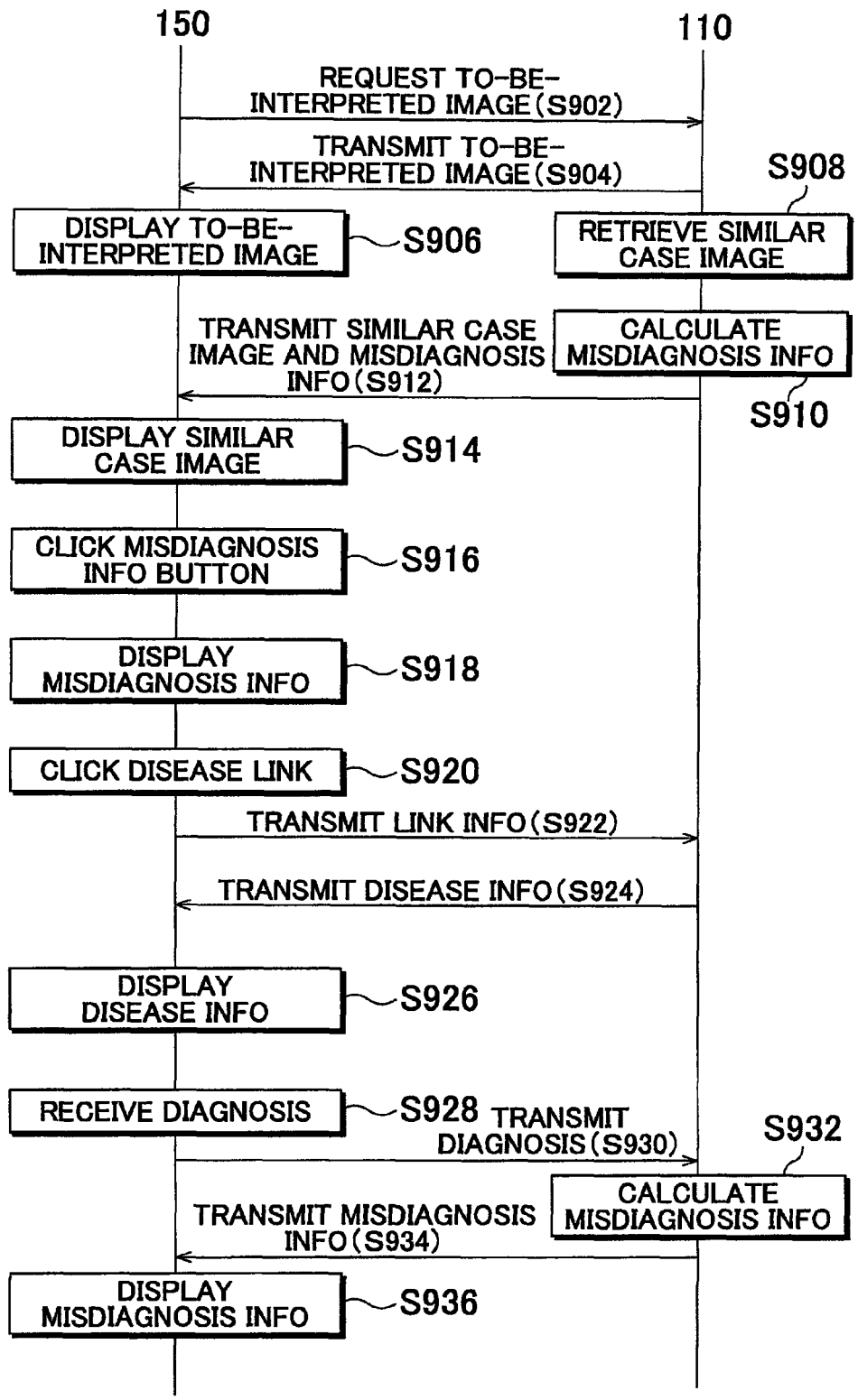
FIG. 9 illustrates an exemplary sequence of operations performed by the radiogram interpreter terminal 150 and medical information processing apparatus 110.

FIG. 9 illustrates an exemplary sequence of operations performed by the radiogram interpreter terminal 150 and medical information processing apparatus 110. The radiogram interpreter terminal 150 requests a to-be-interpreted image which is to be interpreted by the radiogram interpreter 190 (S902). The medical information processing apparatus 110 transmits the requested to-be-interpreted image to the radiogram interpreter terminal 150 (S904). The radiogram interpreter terminal 150 displays the to-be-interpreted image received from the medical information processing apparatus 110 (S906).

The medical information processing apparatus 110 retrieves a similar case image similar to the to-be-interpreted image which has been transmitted to the radiogram interpreter terminal 150 (S908). The operation performed in the step S908 by the medical information processing apparatus 110 is described later in detail with reference to FIG. 10. The medical information processing apparatus 110 calculates misdiagnosis information for each retrieved similar case image (S910). Here, the misdiagnosis information may be data used to display on the radiogram interpreter terminal 150 the misdiagnosis details described with reference to FIG. 8. The medical information processing apparatus 110 then transmits the similar case images retrieved in the step S908 and the misdiagnosis information calculated in the step S910 to the radiogram interpreter terminal 150 (S912).

The radiogram interpreter terminal 150 displays in thumbnails the similar case images in contrast with the to-be-interpreted image, as described with reference to FIG. 7 (S914). When the misdiagnosis information button 760 is clicked with one of the similar case images being selected (S916), the radiogram interpreter terminal 150 displays the misdiagnosis information described with reference to FIG. 8 (S918).

As described with reference to FIGS. 7 and 8, when the disease link is clicked, the radiogram interpreter terminal 150 transmits the link information to the medical information processing apparatus 110 (S922). The medical information processing apparatus 110 reads the linked disease information from the medical information database 130 based on the link information received from the radiogram interpreter terminal 150, and transmits the read disease information to the radiogram interpreter terminal 150 (S924). The radiogram interpreter terminal 150 displays the linked disease information received from the medical information processing apparatus 110 (S926). The disease information displayed on the radiogram interpreter terminal 150 by the medical information processing apparatus 110 is described later with reference to FIG. 13.

When detecting the input of a diagnosis into the diagnosis report input window 730 (S928), the radiogram interpreter terminal 150 transmits the diagnosis including a disease to the medical information apparatus 110 (S930). The medical information processing apparatus 110 calculates misdiagnosis information for the disease included in the input diagnosis as in the step S910 (S932). Note that the misdiagnosis information calculating operation is performed for the disease of the similar case image in the step S910 and for the disease indicated by the diagnosis made by the radiogram interpreter 190 in the step S932. The medical information processing apparatus 110 transmits the misdiagnosis information calculated in the step S932 to the radiogram interpreter terminal 150 (S934). The radiogram interpreter terminal 150 displays the misdiagnosis information as in the step S918 (S936).

Figure 10:
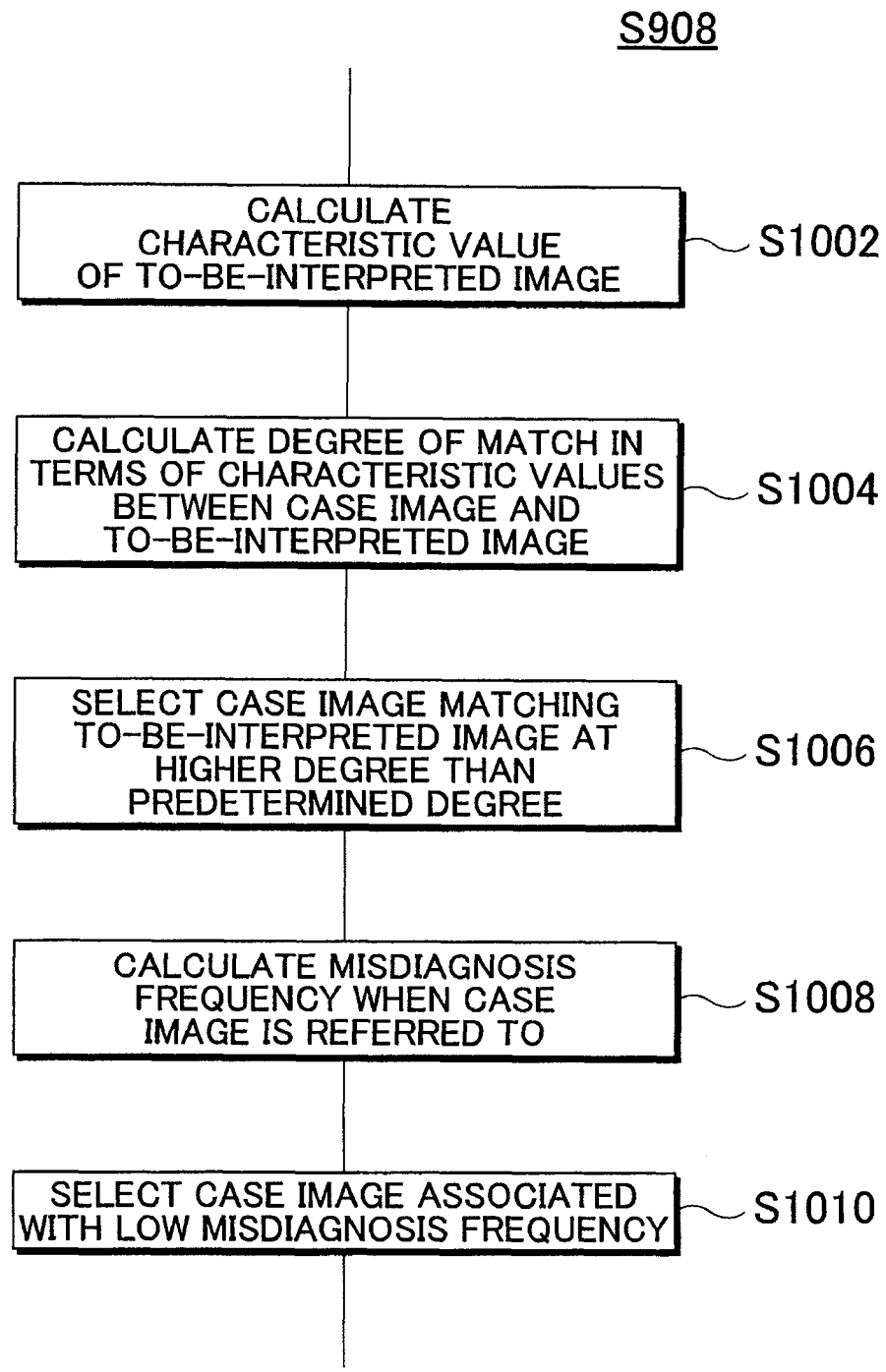
FIG. 10 illustrates an exemplary flow of operations performed by the medical information processing apparatus 110 in a step S908.

FIG. 10 illustrates an exemplary flow of operations performed by the medical information processing apparatus 110 in the step S908. The degree of match calculating section 250 calculates the characteristic value of the to-be-interpreted image (S1002). Here, the characteristic value may include the degree of circularity, the degree of darkness and the size of an abnormal shadow. The abnormal shadow may be a partial image showing a diseased site or suspected diseased site in the image obtained by image-capturing the examinee.

The degree of match calculating section 250 calculates the degree of match in terms of the characteristic values between the abnormal shadow in the to-be-interpreted image and the abnormal shadow in a case image stored on at least one of the medical information database 130 and case database 140 (S1004). The case image selecting section 220 selects a case image including an abnormal shadow matching the abnormal shadow in the to-be-interpreted image at a degree higher than a predetermined degree of match (S1006).

The case image selecting section 220 calculates the frequency information when the selected case image is referred to (S1008). Here, the frequency information calculated in the step SI 008 may indicate the probability of misdiagnosis described with reference to the misdiagnosis information 820 in FIG. 8. The case image selecting section 220 selects a case image whose frequency information calculated in the step S1008 indicates a frequency lower than a predetermined frequency, as a similar case image to be transmitted to the radiogram interpreter terminal 150 (S1010).

FIG. 11 illustrates an exemplary flow of operations performed by the medical information processing apparatus 110 after obtaining an initial diagnosis. The diagnosis obtaining section 200 obtains a disease indicated by an initial diagnosis made at the radiogram interpreter terminal 150 (S1102). The diagnosis obtaining section 200 may obtain the disease directly from the radiogram interpreter terminal 150, or from the diagnosis database 145 or the like.

The index calculating section 280 calculates the degree of unusualness, positive prediction value, negative prediction value and correct diagnosis rate for the disease obtained in the step S1102 (S1104). The index calculating section 280 can calculate, in association with each radiogram interpreter 190 who makes an initial diagnosis, the degree of unusualness, positive prediction value, negative prediction value and correct diagnosis rate, based on the data stored on the diagnosis database 145 described with reference to FIG. 6.

The reliability calculating section 265 calculates the reliability based on the degree of unusualness, positive prediction value, negative prediction value, and correct diagnosis rate which are calculated in the step S1104 (S1106). Specifically speaking, the reliability calculating section 265 calculates the reliability according to the magnitudes of the degree of unusualness, positive prediction value, negative prediction value and correct diagnosis rate. For example, the reliability calculating section 265 may calculate the reliability by adding together the values obtained by multiplying the degree of unusualness, positive prediction value, negative prediction value and correct diagnosis rate which are calculated in the step S1104 by the index calculating section 280 by predetermined weight factors for the degree of unusualness, positive prediction value, negative prediction value and correct diagnosis rate.

The different person judging section 270 judges whether to request a different person to make a diagnosis (S1108). The different person judging section 270 judges that it is necessary to request a different person to make a diagnosis when the reliability calculated in the step S1106 is lower than a predetermined value.

When the different person judging section 270 judges that it is necessary to request a different person to make a diagnosis, the diagnosis-making person selecting section 275 identifies a disease which is likely to be misdiagnosed by an initial diagnosis more than a predetermined value (S1110). Specifically speaking, the diagnosis-making person selecting section 275 identifies a disease indicated by a conclusive diagnosis which is associated on the diagnosis database 145 with the number of cases indicating a higher frequency, from among the conclusive diagnoses which are associated on the diagnosis database 145 with the radiogram interpreter 190 who makes the initial diagnosis and the initial diagnosis and different from the initial diagnosis.

The diagnosis-making person selecting section 275 calculates the degree of unusualness, positive prediction value, negative prediction value and correct diagnosis rate for the disease identified in the step S1110, in association with each of the radiogram interpreters 190 other than the radiogram interpreter 190 who makes the initial diagnosis (S1112). The diagnosis-making person selecting section 275 can calculate, in association with each radiogram interpreter 190, the degree of unusualness, positive prediction value, negative prediction value and correct diagnosis rate, based on the data stored on the diagnosis database 145 described with reference to FIG. 6.

The diagnosis-making person selecting section 275 selects a different radiogram interpreter 190 who is to be requested to make a diagnosis, based on at least one of the degree of unusualness, positive prediction value, negative prediction value and correct diagnosis rate which are calculated in the step S1112 (S1114). Here, the diagnosis-making person selecting section 275 may calculate, in association with each radiogram interpreter 190, the reliability according to the magnitudes of the degree of unusualness, positive prediction value, negative prediction value and correct diagnosis rate, as in the step S1106. For example, the diagnosis-making person selecting section 275 may add together the values obtained by multiplying the degree of unusualness, positive prediction value, negative prediction value and correct diagnosis rate which are calculated in the step S1112 by the index calculating section 280 by predetermined weight factors for the degree of unusualness, positive prediction value, negative prediction value and correct diagnosis rate, in association with each radiogram interpreter 190. The diagnosis-making person selecting section 275 may select a radiogram interpreter 190 who is associated with a larger sum, as the different radiogram interpreter 190 who is to be requested to make a diagnosis.

The output section 210 transmits information identifying the diagnosis-making person selected by the diagnosis-making person selecting section 275 to the radiogram interpreter terminal 150 (S1116). It is assumed that the diagnosis-making person selecting section 275 calculates the reliability with the weight factor for the negative prediction value being set larger than the weight factors for the other indices in the step S1114, for example. With such a setting, when the different radiogram interpreter 190 selected by the diagnosis-making person selecting section 275 diagnoses the examinee as being negative for the disease identified in the step S1110, the examinee is more likely to be negative for the disease. As a result, the medical information processing system 100 can appropriately select a set of radiogram interpreters 190 in such a manner that the reliability can be further enhanced as a whole.

Figure 12:
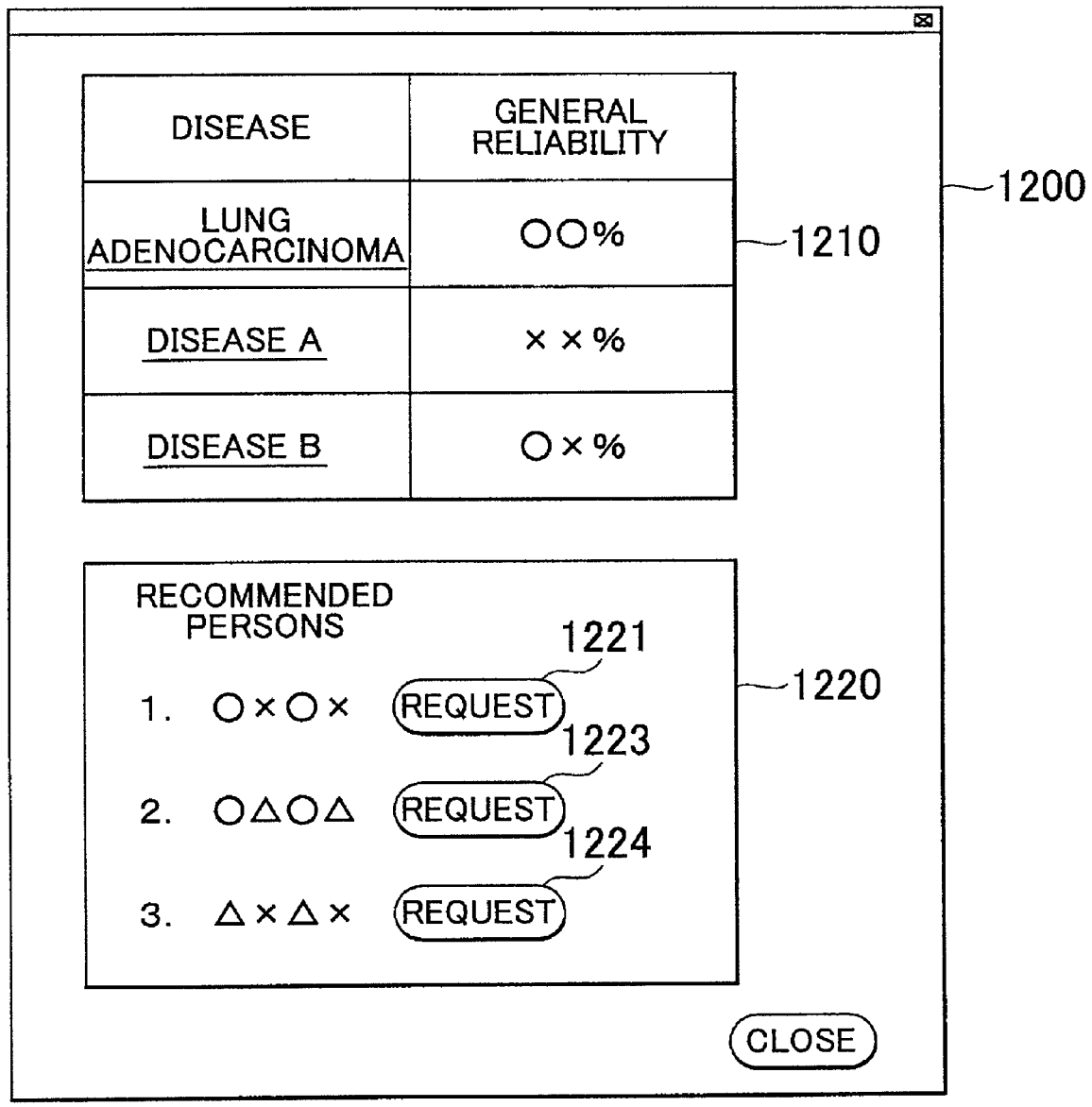
FIG. 12 illustrates an exemplary screen displayed on the radiogram interpreter terminal 150 by the medical information processing apparatus 110.

FIG. 12 illustrates an exemplary screen displayed on the radiogram interpreter terminal 150 by the medical information processing apparatus 110. The medical information processing apparatus 110 causes the radiogram interpreter terminal 150 to display a window 1200 including a reliability field 1210 and a recommended person field 1220. The medical information processing apparatus 110 causes the radiogram interpreter terminal 150 to display a general reliability in association with each disease in the reliability field 1210. Here, the general reliability may be the reliability calculated in the step S1106 by the reliability calculating section 265. The medical information processing apparatus 110 may cause the radiogram interpreter terminal 150 to display the general reliability calculated by the reliability calculating section 265 for a different diagnosis identified by the different diagnosis identifying section 260 in the reliability field 1210, in addition to the reliability of the disease obtained by the diagnosis obtaining section 200.

The medical information processing apparatus 110 may cause the radiogram interpreter terminal 150 to display different radiogram interpreters 190 selected by the diagnosis-making person selecting section 275 in the step S1114 in the recommended person field 1220 as recommended persons to request. The medical information processing apparatus 110 may cause the radiogram interpreter terminal 150 to display request buttons 1221, 1223 and 1224 in association with the respective recommended persons in the recommended person field 1220. When one of the request buttons 1221, 1223 and 1224 is clicked by way of mouse manipulation or the like, the radiogram interpreter terminal 150 transmits, to the medical information processing apparatus 110, information indicating that the corresponding recommended person is to be requested to make a diagnosis. The medical information processing apparatus 110 requests the recommended person received from the radiogram interpreter terminal 150 to make a diagnosis.

FIG. 13 illustrates an example of the disease information displayed on the radiogram interpreter terminal 150 by the medical information processing apparatus 110. When receiving the link information from the radiogram interpreter terminal 150 in the step S922, the medical information processing apparatus 110 reads data indicated by the link information from the medical information database 130 and causes the radiogram interpreter terminal 150 to display a disease information window 1300 including a key point field 1310, a case image field 1320, a differential case image field 1330 and a detailed explanation field 1340.

The medical information database 130 stores key point data including key points to be noticed. The medical information processing apparatus 110 reads the key point data stored on the medical information database 130, generates display data to be displayed in the key point field 1310, and transmits the generated display data to the radiogram interpreter terminal 150. The medical information database 130 also stores case images 1321 to 1324. The medical information processing apparatus 110 reads the case images 1321 to 1324 stored on the medical information database 130, generates display data to be displayed in the case image field 1320, and transmits the generated display data to the radiogram interpreter terminal 150.

The medical information database 130 also stores case images 1331 to 1335 of different diseases which may present similar shadows. The medical information processing apparatus 110 reads the case images 1331 to 1335 stored on the medical information database 130, generates display data to be displayed in the differential case image field 1330, and transmits the generated display data to the radiogram interpreter terminal 150. The medical information database 130 also stores detailed explanation data including the general overview of the disease, pathological findings, key points to be noticed when watching images, and the like. The medical information processing apparatus 110 reads the detailed explanation data stored on the medical information database 130, generates display data to be displayed in the detailed explanation field 1340, and transmits the generated display data to the radiogram interpreter terminal 150.

What is displayed in a selected area of the disease information window 1300 is electronically duplicable by way of the mouse manipulation of the radiogram interpreter 190 or the like. The duplicated information can be input into the diagnosis report input window 730 by mouse manipulation or the like. For example, by clicking or selecting the information "○□ is found" displayed under the images 1321 to 1324 by way of mouse manipulation, the information is duplicated in the memory of the radiogram interpreter terminal 150, and the duplicated information can be easily input into the diagnosis report input window 730 by way of mouse manipulation or the like.

As described above, the medical information processing system 100 can appropriately provide misdiagnosis information when the radiogram interpreter 190 makes a diagnosis. Therefore, the present embodiment can be expected to increase the reliability of the diagnosis. In addition, the medical information processing system 100 can make use of the information stored on the medical information database 130 and the diagnoses stored on the case database 140. Therefore, the present embodiment can be expected to lower the probability of inputting errors. Furthermore, after a given radiogram interpreter 190 has made a diagnosis, the medical information processing system 100 can recommend a different radiogram interpreter 190 appropriately in accordance with the radiogram interpretation by the given radiogram interpreter 190. Therefore, the present embodiment can be expected to enhance the reliability of the diagnoses as a whole.

Figure 14:
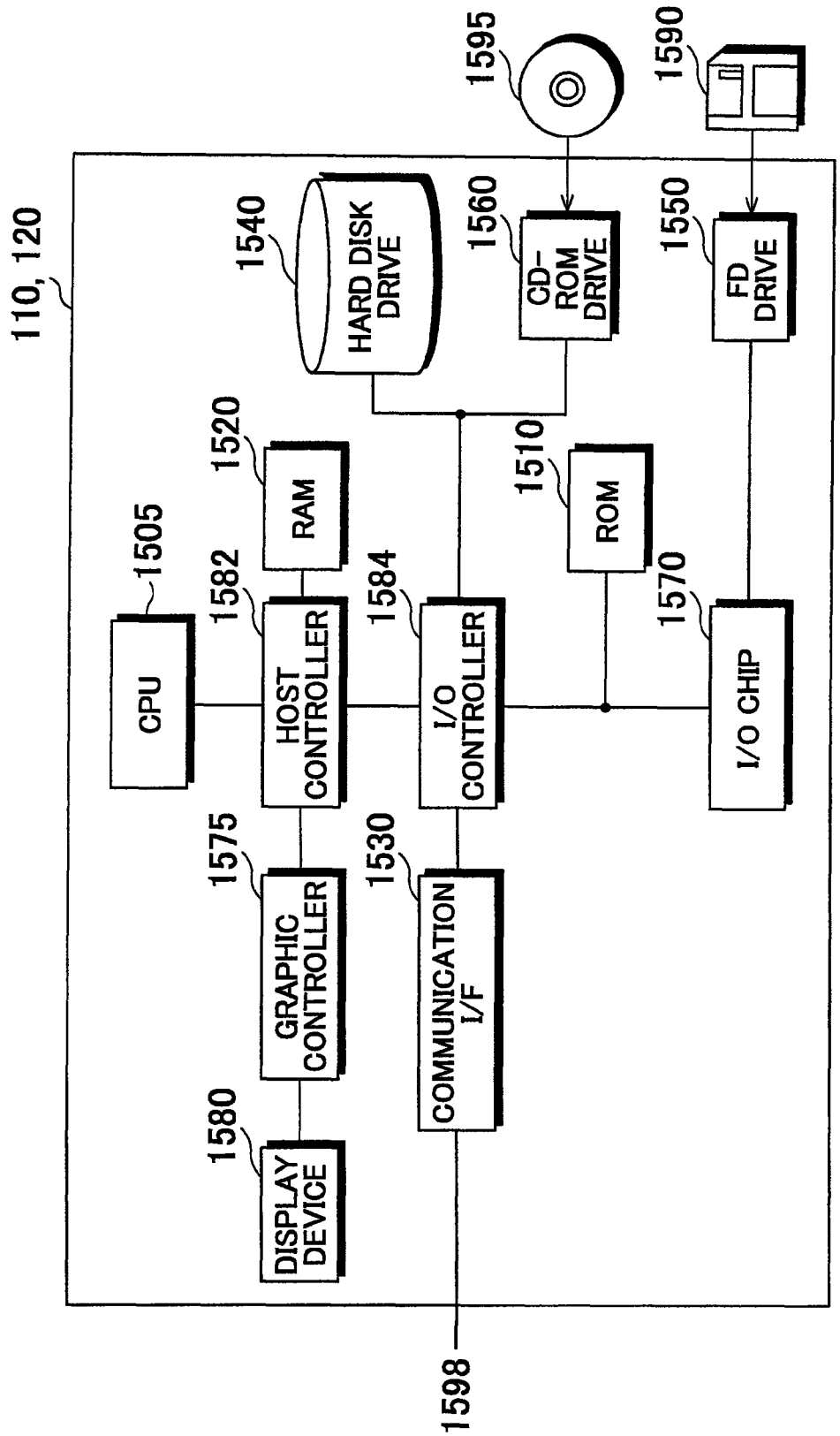
FIG. 14 illustrates an exemplary hardware configuration of an electronic information processing apparatus such as a computer which implements the medical information processing apparatus 110 and diagnosis assistance information database 120.

FIG. 14 illustrates an exemplary hardware configuration of an electronic information processing apparatus such as a computer which implements the medical information processing apparatus 110 and diagnosis assistance information database 120. The medical information processing apparatus 110 and diagnosis assistance information database 120 are constituted by a CPU surrounding section, an input/output (I/O) section and a legacy I/O section. The CPU surrounding section includes a CPU 1505, a RAM 1520, a graphic controller 1575, and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520 at a high transfer rate. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon image data generated by the CPU 1505 or the like.

The I/O controller 1584 connects, to the host controller 1582, the hard disk drive 1540, communication interface 1530 and CD-ROM drive 1560 which are I/O devices operating at a relatively high rate. The hard disk drive 1540 stores thereon programs and data to be used by the CPU 1505. The communication interface 1530 couples to the network communication apparatus 1598, to transmit/receive programs or data. The CD-ROM drive 1560 reads programs or data from a CD-ROM 1595, and supplies the read programs or data to the hard disk drive 1540 and communication interface 1530 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the medical information processing apparatus 110 and the diagnosis assistance information database 120 at the start up, programs dependent on the hardware of the medical information processing apparatus 110 and the diagnosis assistance information database 120, and the like. The flexible disk drive 1550 reads programs or data from a flexible disk 1590, and supplies the read programs or data to the hard disk drive 1540 and communication interface 1530 via the RAM 1520. The I/O chip 1570 is used to connect a variety of I/O devices such as the flexible disk drive 1550 via, for example, a parallel port, a serial port, a keyboard port, a mouse port or the like.

The program to be executed by the CPU 1505 is provided by a user in the state of being stored on a recording medium such as the flexible disk 1590, the CD-ROM 1595, and an IC card. The program may be stored on the recording medium in the state of being compressed or not being compressed. The program is installed from the recording medium onto the hard disk drive 1540, read by the RAM 1520, and executed by the CPU 1505. The program executed by the CPU 1505 causes the medical information processing apparatus 110 to function as the diagnosis obtaining section 200, diagnosis receiving section 205, output section 210, case image selecting section 220, to-be-diagnosed image obtaining section 230, reference case image identifying section 240, frequency information updating section 245, degree of match calculating section 250, different diagnosis identifying section 260, reliability calculating section 265, different person judging section 270, diagnosis-making-person selecting section 275, and index calculating section 280 described with reference to FIGS. 1 to 13, and causes the diagnosis assistance information database 120 to function as the diagnosis assistance information database 120 described with reference to FIGS. 1 to 13.

The program mentioned above may be stored on an external recording medium. The recording medium is, for example, an optical recording medium such as DVD and PD, a magnet-optical recording medium such as MD, a tape medium, a semiconductor memory such as an IC card and the like, in addition to the flexible disk 1590 and CD-ROM 1595. The recording medium may be a storage device such as a hard disk or RAM which is provided in a server system connected to a dedicated communication network or the Internet, and the program may be provided to the medical information processing apparatus 110 and the diagnosis assistance information database 120 via the network.

Although some aspects of the present invention have been described by way of exemplary embodiments, it should be understood that those skilled in the art might make many changes and substitutions without departing from the spirit and the scope of the present invention which is defined only by the appended claims.

What is claimed is:

1. A medical information processing system comprising:
a diagnosis information storing section configured to store one or more combinations of an initial diagnosis and a conclusive diagnosis and stores frequency information indicating a frequency with which each combination is observed and frequency information indicating a frequency with which a combination of an initial diagnosis disease indicated by the initial diagnosis and a conclusive diagnosis disease indicated by the conclusive diagnosis that is different from the initial diagnosis disease is observed, in association with the initial diagnosis disease and the conclusive diagnosis disease;
a diagnosis receiving section configured to receive a diagnosis during a diagnosis process; and
a disease information presenting section configured to i) if the received diagnosis is the same as an initial diagnosis stored in the diagnosis information storing section, output, according to the frequency information, one or more of the conclusive diagnoses stored in combination with the initial diagnosis, and ii) if the received diagnosis is the same as a conclusive diagnosis stored in the diagnosis information storing section, output according to the frequency information, one or more of the initial diagnoses stored in combination with the conclusive diagnosis,
wherein the initial diagnosis is based on a possible condition and the conclusive diagnosis is based on an actual condition,
wherein a conclusive diagnosis is a diagnosis indicating whether a disease is present and what type a disease belongs to, and
wherein the frequency information indicates a number of combinations in which the initial diagnosis and the conclusive diagnosis are different.

2. The medical information processing system as set forth in claim 1, wherein
the diagnosis receiving section is configured to receive disease whose disease information is to be presented during the diagnosis process, and
the disease information presenting section is configured to present disease information of the conclusive diagnosis disease which is stored on the diagnosis information storing section in association with the initial diagnosis disease that is the same as the disease received by the diagnosis receiving section, in a manner according to the frequency information.

3. The medical information processing system as set forth in claim 2, wherein
the diagnosis information storing section is configured to store thereon the frequency information further in association with a finding observed during a diagnosis process, and
the disease information presenting section is configured to present a finding for the conclusive diagnosis disease which is stored on the diagnosis information storing section in association with the initial diagnosis disease that is the same as the disease received by the diagnosis receiving section, in a manner according to the frequency information.

4. The medical information processing system as set forth in claim 2, wherein
the diagnosis information storing section is configured to store thereon the frequency information further in association with a symptom observed during a diagnosis process, and
the disease information presenting section is configured to present a symptom of the conclusive diagnosis disease which is stored on the diagnosis information storing section in association with the initial diagnosis disease that is the same as the disease received by the diagnosis receiving section, in a manner according to the frequency information.

5. The medical information processing system as set forth in claim 2, wherein
the diagnosis receiving section is configured to receive a disease relating to a diagnosis target which is to be diagnosed during the diagnosis process.

6. The medical information processing system as set forth in claim 5, further comprising:
a case image storing section configured to store thereon case images to be presented during a diagnosis process; and
a case image selecting section configured to select a case image to be referred during the diagnosis process, from the case images stored on the case image storing section, wherein
the diagnosis receiving section is configured to receive a disease indicated by the case image selected by the case image selecting section.

7. The medical information processing system as set forth in claim 6, wherein
from the case images stored on the case image storing section, the case image selecting section is configured to select the case image that matches, in terms of characteristic values, a to-be-diagnosed image at a degree higher than a predetermined degree of match.

8. The medical information processing system as set forth in claim 7, further comprising
a reference case image identifying section configured to identify a case image referred to to make an initial diagnosis, wherein
the diagnosis information storing section is configured to store thereon the frequency information in association with the referred case image identified by the reference case image identifying section, the initial diagnosis disease and the conclusive diagnosis disease, and
the disease information presenting section is configured to present one of the conclusive diagnosis disease and the initial diagnosis disease which is stored on the diagnosis information storing section in association with the case image identified by the reference case image identifying section and one of the initial diagnosis disease and the conclusive diagnosis disease which is the same as the disease received by the diagnosis receiving section, in a manner according to the frequency information, and presents the case image selected by the case image selecting section.

9. The medical information processing system as set forth in claim 8, wherein
from the case images stored on the case image storing section, the case image selecting section is configured to select the case image that (i) matches, in terms of characteristic values, a to-be-diagnosed image at a degree higher than a predetermined degree of match and (ii) is stored in association with frequency information satisfying a predetermined condition on the diagnosis information storing section.

10. The medical information processing system as set forth in claim 9, wherein
from the case images stored on the case image storing section, the case image selecting section is configured to select the case image that (i) matches, in terms of the characteristic values, the to-be-diagnosed image at the degree higher than the predetermined degree of match and (ii) is stored in association with the frequency information indicating a lower frequency than a predetermined value on the diagnosis information storing section.

11. The medical information processing system as set forth in claim 5, further comprising:
a case image storing section configured to store thereon case images to be presented during a diagnosis process; and
a case image selecting section configured to select a case image to be referred to during the diagnosis process, from the case images stored on the case image storing section, wherein
the diagnosis receiving section is configured to receive a finding made for an examinee whose case image is selected by the case image selecting section, and
the disease information presenting section is configured to present the disease information of the conclusive diagnosis disease that is stored on the diagnosis information storing section in association with the initial diagnosis disease that is the same as a disease indicated by the finding received by the diagnosis receiving section, in a manner according to the frequency information.

12. The medical information processing system as set forth in claim 5, further comprising:
a case image storing section configured to store thereon case images to be presented during a diagnosis process; and
a case image selecting section configured to select a case image to be referred to during the diagnosis process, from the case images stored on the case image storing section, wherein
the diagnosis receiving section is configured to receive a symptom observed for an examinee whose case image is selected by the case image selecting section, and
the disease information presenting section is configured to present the disease information of the conclusive diagnosis disease that is stored on the diagnosis information storing section in association with the initial diagnosis disease that is the same as a disease indicated by the symptom received by the diagnosis receiving section, in a manner according to the frequency information.

13. The medical information processing system as set forth in claim 2, wherein
the diagnosis receiving section is configured to receive a finding, and
the disease information presenting section is configured to present the disease information of the conclusive diagnosis disease that is stored on the diagnosis information storing section in association with the initial diagnosis disease that is the same as a disease indicated by the finding received by the diagnosis receiving section, in a manner according to the frequency information.

14. The medical information processing system as set forth in claim 2, wherein the diagnosis receiving section is configured to receive a symptom observed during the diagnosis process, and the disease information presenting section is configured to present the disease information of the conclusive diagnosis disease that is stored on the diagnosis information storing section in association with the initial diagnosis disease that is the same as a disease indicated by the symptom received by the diagnosis receiving section, in a manner according to the frequency information.

15. The medical information processing system as set forth in claim 2, wherein when the diagnosis information storing section is configured to store thereon a plurality of conclusive diagnosis diseases in association with the initial diagnosis disease that is the same as the disease received by the diagnosis receiving section, the disease information presenting section is configured to increase degrees of emphasis on a plurality of pieces of disease information of the plurality of conclusive diagnosis diseases as frequencies indicated by a plurality of pieces of frequency information associated with the plurality of conclusive diagnosis diseases increase, when presenting the plurality of pieces of disease information.

16. The medical information processing system as set forth in claim 1, further comprising:

a diagnosis obtaining section configured to obtain a new conclusive diagnosis; and a frequency information updating section that, when the diagnosis obtaining section obtains the new conclusive diagnosis, is configured to calculate the frequency, and updates the frequency information that is stored on the diagnosis information storing section in association with the conclusive diagnosis and the initial diagnosis with frequency information indicating the calculated frequency.

17. The system of claim 1, wherein the frequency information is representative of a probability of mistaken diagnosis based on combinations of initial and conclusive diagnoses.

18. The medical information processing system as set forth in claim 1, wherein the diagnosis information storing section is configured to store sameness information indicating the frequency with which initial diagnoses made by a diagnosis-making person are the same as conclusive diagnoses, in association with a diagnosis-making person, and further comprising:

a reliability calculating section configured to calculate reliability for the diagnosis-making person based on the sameness information; and a diagnosis assistance information generating section configured to judge whether it is necessary to request a different diagnosis-making person to make another diagnosis based on the calculated reliability.

19. A medical information processing method comprising: providing a processor and memory for:

storing in the memory one or more combinations of an initial diagnosis and a conclusive diagnosis and frequency information indicating a frequency with which combination is observed and frequency information indicating a frequency with which a combination of an initial diagnosis disease indicated by the initial diagnosis and a conclusive diagnosis disease indicated by the conclusive diagnosis that is different from the initial diagnosis disease is observed, in association with the initial diagnosis disease and the conclusive diagnosis disease;

receiving a diagnosis during a diagnosis process; and presenting one of the conclusive diagnosis and the initial diagnosis, wherein i) if the received diagnosis is the same as an initial diagnosis stored in the memory, presenting, according to frequency information, one or more of the conclusive diagnoses stored in combination with the initial diagnosis, and if ii) the received diagnosis is the same as a conclusive diagnosis stored in the memory, presenting, according to the frequency information, one or more of the initial diagnoses stored in combination with the conclusive diagnosis, wherein the initial diagnosis is based on a possible condition and the conclusive diagnosis is based on an actual condition, and wherein the frequency information indicates a number of combinations in which the initial diagnosis and the conclusive diagnosis are different.

20. A non-transitory computer readable medium storing thereon a program for use with a medical information processing system, the program causing the medical information processing system to function as:

a diagnosis information storing section configured to store one or more combinations of an initial diagnosis and a conclusive diagnosis and stores frequency information indicating a frequency with which each combination is observed and frequency information indicating a frequency with which a combination of an initial diagnosis disease indicated by the initial diagnosis and a conclusive diagnosis disease indicated by the conclusive diagnosis that is different from the initial diagnosis disease is observed, in association with the initial diagnosis disease and the conclusive diagnosis disease;

a diagnosis receiving section configured to receive a diagnosis during a diagnosis process; and a disease information presenting section that, i) if the received diagnosis is the same as an initial diagnosis stored in the diagnosis information storing section, is configured to output, according to the frequency information, one or more of the conclusive diagnoses stored in combination with the initial diagnosis, and ii) if the received diagnosis is the same as a conclusive diagnosis stored in the diagnosis information storing section, is configured to output according to the frequency information, one or more of the initial diagnoses stored in combination with the conclusive diagnosis, wherein the initial diagnosis is based on a possible condition and the conclusive diagnosis is based on an actual condition, and wherein the frequency information indicates a number of combinations in which the initial diagnosis and the conclusive diagnosis are different.

\* \* \* \* \*